(12) United States Patent
Biener et al.

(10) Patent No.: US 12,102,760 B2
(45) Date of Patent: Oct. 1, 2024

(54) PATIENT INTERFACE

(71) Applicant: ResMed Pty Ltd, Bella Vista (AU)

(72) Inventors: Achim Biener, Aufkirchen (DE); Christian Bayer, Penzberg (DE); Fred Komorowski, Munich (DE); Bernd Christoph Lang, Graefelfing (DE)

(73) Assignee: ResMed Pty Ltd, Bella Vista (AU)

( * ) Notice: Subject to any disclaimer, the term of this patent is extended or adjusted under 35 U.S.C. 154(b) by 1024 days.

(21) Appl. No.: 17/003,000

(22) Filed: Aug. 26, 2020

(65) Prior Publication Data

US 2020/0384232 A1 Dec. 10, 2020

Related U.S. Application Data

(63) Continuation of application No. 15/308,163, filed as application No. PCT/AU2015/050199 on Apr. 28, 2015, now Pat. No. 10,786,643.

(30) Foreign Application Priority Data

May 1, 2014 (AU) .................................. 2014901585

(51) Int. Cl.
*A61M 16/06* (2006.01)
*A61M 16/00* (2006.01)
(Continued)

(52) U.S. Cl.
CPC .... *A61M 16/0666* (2013.01); *A61M 16/0066* (2013.01); *A61M 16/0672* (2014.02);
(Continued)

(58) Field of Classification Search
CPC .............. A61M 16/0066; A61M 16/06; A61M 16/0666; A61M 16/0672; A61M 16/0683;
(Continued)

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

CN 1988930 A 6/2007
JP 2006-518231 A 8/2006
(Continued)

OTHER PUBLICATIONS

Office Action dated Aug. 29, 2022 issued in Japanese Application No. 2021-161283 with English translation (21 pages).
(Continued)

*Primary Examiner* — Joshua Lee
(74) *Attorney, Agent, or Firm* — Nixon & Vanderhye P.C.

(57) ABSTRACT

A patient interface comprises a frame, a headgear, a manifold and two nasal prongs. The frame may be recessed from the face of the patient, and preferably from the manifold so that the manifold may deform or move with respect to the face of the patient. The manifold may be further configured to be compliant in the direction of engagement with the patient's face, such as in the anterior direction. These features may allow the manifold to engage with the face of the patient, such as the upper lip, without exerting a significant pressure which may lead to patient discomfort. The manifold may also be configured to be rotatable with respect to the frame, for example by a grip feature which may be configured to be held in one hand for rotation.

6 Claims, 31 Drawing Sheets

(51) Int. Cl.
  *A61M 16/16* (2006.01)
  *A61M 16/08* (2006.01)
  *A61M 16/10* (2006.01)

(52) U.S. Cl.
  CPC ........ *A61M 16/0683* (2013.01); *A61M 16/16* (2013.01); *A61M 2016/0027* (2013.01); *A61M 16/06* (2013.01); *A61M 16/0816* (2013.01); *A61M 16/107* (2014.02); *A61M 2205/42* (2013.01); *A61M 2205/50* (2013.01)

(58) Field of Classification Search
  CPC ............ A61M 16/0816; A61M 16/107; A61M 16/16; A61M 2016/0027; A61M 2205/42; A61M 2205/50
  See application file for complete search history.

(56) References Cited

U.S. PATENT DOCUMENTS

| | | | |
|---|---|---|---|
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 9,072,855 | B2 * | 7/2015 | McAuley .......... A61M 16/0622 |
| 9,604,025 | B2 | 3/2017 | Pastoor et al. |
| 10,376,666 | B2 * | 8/2019 | McAuley .......... A61M 16/0616 |
| 10,828,449 | B2 * | 11/2020 | Higgins ............ A61M 16/0666 |
| 2004/0226566 | A1 | 11/2004 | Gunaratnam |
| 2005/0028822 | A1 | 2/2005 | Sleeper et al. |
| 2005/0241644 | A1 | 11/2005 | Gunaratnam et al. |
| 2006/0124131 | A1 | 6/2006 | Chandran et al. |
| 2006/0231103 | A1 | 10/2006 | Matula et al. |
| 2008/0245369 | A1 | 10/2008 | Matula et al. |
| 2009/0044808 | A1 | 2/2009 | Guney et al. |
| 2009/0050156 | A1 | 2/2009 | Ng et al. |
| 2009/0145429 | A1 | 6/2009 | Ging et al. |
| 2009/0151729 | A1 | 6/2009 | Judson et al. |
| 2009/0173349 | A1 | 7/2009 | Hernandez et al. |
| 2010/0000534 | A1 | 1/2010 | Kooij et al. |
| 2010/0108073 | A1 | 5/2010 | Zollinger et al. |
| 2010/0229868 | A1 | 9/2010 | Rummery |
| 2011/0023874 | A1 | 2/2011 | Bath |
| 2011/0067704 | A1 | 3/2011 | Kooij et al. |
| 2011/0146685 | A1 | 6/2011 | Allan et al. |
| 2011/0265796 | A1 | 11/2011 | Amarasinghe et al. |
| 2012/0090622 | A1 | 4/2012 | Chang |
| 2012/0204870 | A1 * | 8/2012 | McAuley .......... A61M 16/0666 128/207.18 |
| 2013/0008447 | A1 | 1/2013 | Gunaratnam |
| 2016/0256653 | A1 * | 9/2016 | McAuley .......... A61M 16/0875 |
| 2017/0049984 | A1 | 2/2017 | Biener et al. |
| 2019/0298957 | A1 * | 10/2019 | McAuley .......... A61M 16/0616 |

FOREIGN PATENT DOCUMENTS

| | | |
|---|---|---|
| JP | 2007-532155 A | 11/2007 |
| JP | 2009-517185 A | 4/2009 |
| JP | 2013-521845 | 6/2013 |
| JP | 2013-538658 A | 10/2013 |
| JP | 2017-514599 A | 6/2017 |
| WO | WO 98/04310 A1 | 2/1998 |
| WO | WO 98/34665 A1 | 8/1998 |
| WO | WO 00/78381 A1 | 12/2000 |
| WO | WO 2004/073778 A1 | 9/2004 |
| WO | WO 2005/063328 A1 | 7/2005 |
| WO | WO 2005/097247 A1 | 10/2005 |
| WO | WO 2006/074513 A1 | 7/2006 |
| WO | WO 2006/130903 A1 | 12/2006 |
| WO | WO 2008/014543 A1 | 2/2008 |
| WO | WO 2009/052560 A1 | 4/2009 |
| WO | WO 2010/135785 A1 | 12/2010 |
| WO | WO 2011/062510 A1 | 5/2011 |
| WO | WO 2012/171072 A1 | 12/2012 |
| WO | WO 2013/020167 A1 | 2/2013 |
| WO | WO 2013/042004 A1 | 3/2013 |
| WO | WO 2013/072797 A1 | 5/2013 |
| WO | 2014/015382 A1 | 1/2014 |

OTHER PUBLICATIONS

Office Action dated May 31, 2021 issued in Japanese Application No. 2019-193541 with English translation (5 pages).
Notice of Allowance dated Nov. 8, 2021 issued in Japanese Application No. 2019-193541 (3 pages).
Office Action dated Nov. 12, 2021 issued in Chinese Application No. 201910972806.X with English Translation (15 pages).
Extended European Search Report dated Oct. 12, 2020 issued in European Application No. 20180567.8 (9 pages).
Office Action dated Dec. 14, 2020 issued in Japanese Application No. 2019-193541 with English translation (11 pages).
Notice of Reasons for Rejection mailed Jan. 21, 2019 in Japanese Application No. 2016-565426, with English translation, 10 pages.
First Amended Notice of Opposition to Grant of Patent filed Jun. 22, 2016 in New Zealand Application No. 630742 (4 pages).
Deadline for Counterstatement mailed by IPONZ in New Zealand Appln. No. 630742 (2 pages) with Baldwins Law Limited Cover Letter dated Aug. 13, 2018 (1 page), including Second Amended Statement of Case dated Aug. 13, 2018 and filed by Fisher & Paykel Healthcare Limited in New Zealand Appln. No. 630742 (12 pages)(15 pages total).
Baldwins Law Limited cover letter filed Sep. 19, 2018 in New Zealand Appln. No. 630742 with Third Amended Statement of Case (Clean and Tracked Versions) dated Sep. 13, 2018 (25 pages).
First Office Action mailed Jul. 30, 2018 in Chinese Application No. 201580036450.9, with English translation (10 pages).
Extended European Search Report mailed Dec. 8, 2017 in European Application No. 15785668.3 (9 pages).
West, John B., "Respiratory Physiology", Lippincott Williams & Wilkins, 9th edition published 2012, 8 pages
International Search Report for PCT/AU2015/050199 mailed Jul. 27, 2015, 7 pages.
Written Opinion of the ISA for PCT/AU2015/050199 mailed Jul. 27, 2015, 7 pages.
International Preliminary Report on Patentability for PCT/AU2015/050199 dated Jun. 17, 2016, 13 pages.
Notification of Grant dated Jun. 6, 2022 issued in Chinese Application No. 201910972806.X (4 pages).
Office Action dated Jan. 15, 2024 issued in Japanese Application No. 203-067944 with English translation (8 pages).
Office Action dated Jun. 24, 2024 issued in Japanese Application No. 2023-067944 with English translation (4 pages).

* cited by examiner

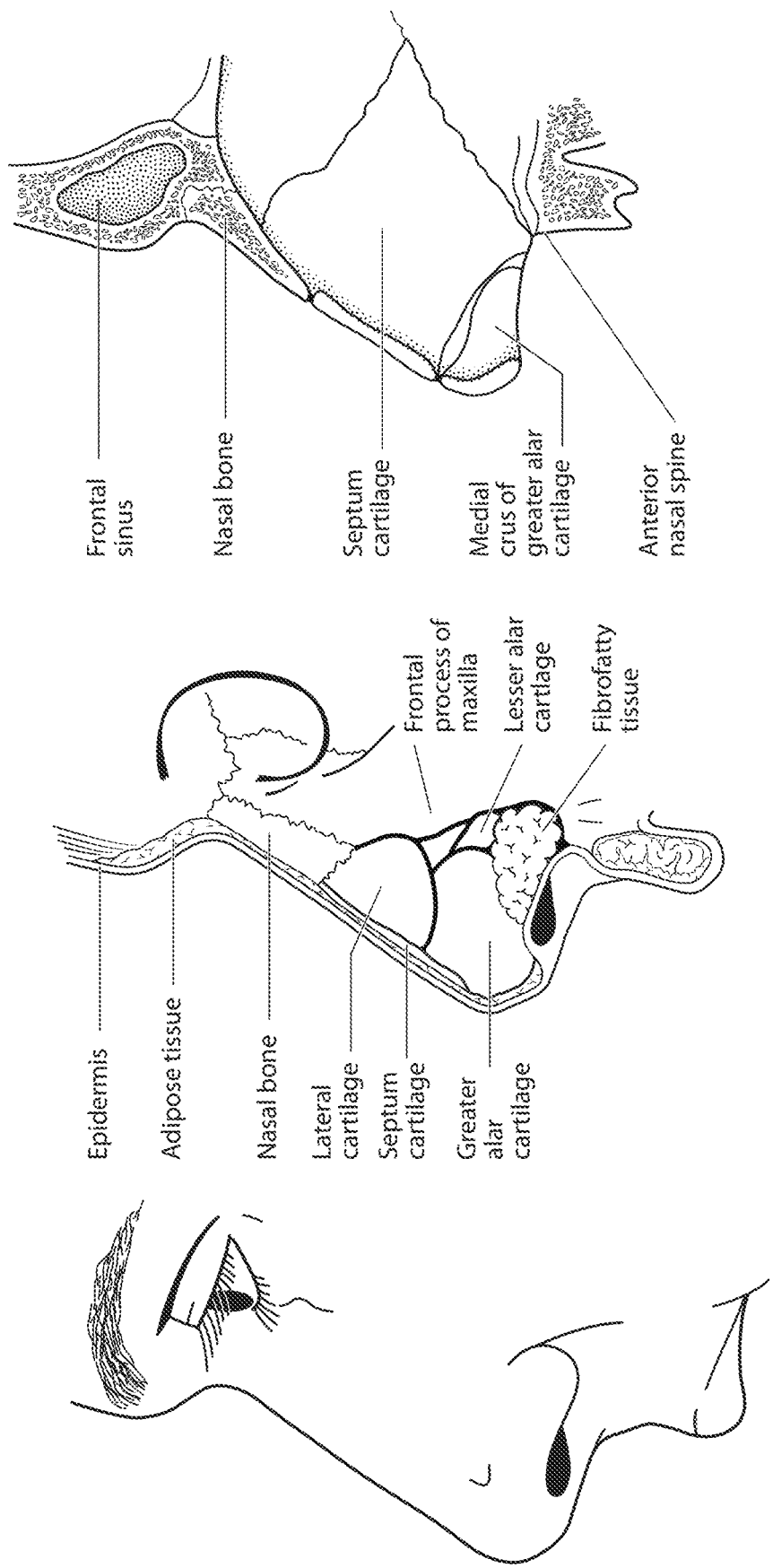

PATIENT INTERFACE

1 CROSS-REFERENCE TO RELATED APPLICATIONS

This application is a continuation of U.S. application Ser. No. 15/308,163, filed Nov. 1, 2016, now allowed, which is the U.S. national phase of International Application No. PCT/AU2015/050199 filed Apr. 28, 2015 which designated the U.S. and claims the benefit of Australian Provisional Patent Application No. AU 2014901585, filed May 1, 2014, the entire contents of each of which are incorporated herein by reference.

2 BACKGROUND OF THE INVENTION

2.1 Field of the Invention

The present technology relates to one or more of the detection, diagnosis, treatment, prevention and amelioration of respiratory-related disorders. In particular, the present technology relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2011.

A range of respiratory disorders exist. Such disorders may be characterised by particular events, e.g. apneas, hypopneas, and hypopneas.

Obstructive Sleep Apnea (OSA), a form of Sleep Disordered Breathing (SDB), is characterized by events comprising occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. NIV has been used to treat CSR, OHS, COPD, MD and Chest Wall disorders.

Invasive ventilation (IV) provides ventilatory support to patients that are no longer able to effectively breathe themselves and may be provided using a tracheostomy tube.

High-flow therapy provides a flow of breathable gas (e.g. air, oxygen or oxygen-enriched air) at a 'high' flow rates, such as up to 60 L/min. To deliver breathable gases at the required high flow rates, HFT is typically carried out through nasal cannula. HFT has been used to reduce the work of breathing and to promote gas exchange.

Ventilators may control the timing and pressure of breaths pumped into the patient and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

2.2.3 Treatment Systems

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its user, for example by providing a flow of air. The flow of air may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cm H2O. For other forms of therapy, such as the delivery of oxygen, or high-flow therapy, the patient interface may not include a seal sufficient to facilitate delivery to the airways of a supply of gas at a positive pressure of about 10 cm H2O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, mask designed as part of personal protection equipment (e.g. filter masks), SCUBA masks, or for the administration of anaesthetics may be tolerable for their original application, but nevertheless be undesirably uncomfortable to be worn for extended periods of time, e.g. several hours. This is even more so if the mask is to be worn during sleep.

Nasal CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g. difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, masks for delivery of nasal CPAP during sleep form a distinct field.

2.2.3.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be in appropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may unintentionally leak. Furthermore, if the shape of the seal-forming portion does not match that of the patient, it may crease or buckle in use, giving rise to unintentional leaks.

Another type of seal-forming portion may comprise a friction-fit element, e.g. for insertion into a naris.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063,328 and WO 2006/130,903 (describing amongst other things aspects of ResMed LIBERTY full-face mask); International Patent Application WO 2009/052,560 (describing amongst other things aspects of ResMed SWIFT FX nasal pillows).

2.2.3.1.2 Positioning and Stabilising

A seal-forming portion of a patient interface used for positive air pressure therapy is subject to the corresponding force of the air pressure to disrupt a seal.

Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

It may be desirable to retain the patient interface in its operating orientation and/or location during use, for either or both the sealing (a nasal pillows) and/or the non-sealing (e.g. a nasal cannula) type. Retention of the patient interface in its operating orientation and/or location may in turn allow the patient interface to maintain a seal and/or to effectively deliver breathable gases (e.g. oxygen) to the patient.

In use, a patient interface may be subject to forces that tend to displace the patient interface from its operating orientation and/or location. For example, the patient interface in use may be pulled by one or more of: its own weight, weight of an air circuit, tension in the air circuit and any friction between the patient interface and another object, such as a surface of a bed.

Thus, a positioning and stabilising structure may be used to maintain a seal and/or to maintain a patient interface in its operating orientation and/or location.

2.2.3.1.3 Vent Technologies

Some forms of patient interface systems may include a vent to allow the washout of exhaled carbon dioxide. The vent may allow a flow of gas from an interior space of the patient interface, e.g. the plenum chamber, to an exterior of the patient interface, e.g. to ambient. The vent may comprise an orifice and gas may flow through the orifice in use of the mask. Many such vents are noisy. Others may block in use and provide insufficient washout. Some vents may be disruptive of the sleep of a bed-partner 1100 of the patient 1000, e.g. through noise or focussed airflow.

ResMed Limited has developed a number of improved mask vent technologies. See WO 1998/034,665; WO 2000/078,381; U.S. Pat. No. 6,581,594; US Patent Application; US 2009/0050156; US Patent Application 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |

(* one specimen only, measured using test method specified in ISO3744 in CPAP mode at 10 cmH$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

Some forms of patient interfaces may not include a vent. One example of non-vented patient interfaces includes those designed for use with dual-limb air circuits, which may include an expiratory limb for transporting exhaled gases (e.g. carbon dioxide) away from the patient. Another example may be a non-sealed patient interface, such as a nasal cannula. In some nasal cannulae, exhaled gases may be transported away from the patient through the one or more gaps created between the patient interface and the patient's airways.

2.2.3.2 Respiratory Pressure Therapy (RPT) Device

One known RPT device used for treating sleep disordered breathing is the S9 Sleep Therapy System, manufactured by ResMed. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

RPT devices typically also include an inlet filter, various sensors, and a microprocessor-based controller. A blower may include a servo-controlled motor, a volute, and an impeller. In some cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the pressure generator may also include a valve capable of discharging generated air to atmosphere as a means for altering the pressure delivered to the patient as an alternative to motor speed control. The sensors measure, amongst other things, motor speed, mass flow rate and outlet pressure, such as with a pressure transducer or the like. The controller may include data storage capacity with or without integrated data retrieval and display functions.

| Table of noise output levels of prior RPT devices (one specimen only, measured using test method specified in ISO3744 in CPAP mode at 10 cmH₂O). | | |
| --- | --- | --- |
| RPT Devicename | A-weighted sound power level dB(A) | Year (approx.) |
| C-Series Tango | 31.9 | 2007 |
| C-Series Tango with Humidifier | 33.1 | 2007 |
| S8 Escape II | 30.5 | 2005 |
| S8 Escape II with H4i Humidifier | 31.1 | 2005 |
| S9 AutoSet | 26.5 | 2010 |
| S9 AutoSet with H5i Humidifier | 28.6 | 2010 |

2.2.3.3 Humidifier

Delivery of a flow of air without humidification may cause drying of airways. Medical humidifiers are used to increase humidity and/or temperature of the flow of air in relation to ambient air when required, typically where the patient may be asleep or resting (e.g. at a hospital). As a result, a medical humidifier may be small for bedside placement, and it may be configured to only humidify and/or heat the flow of air delivered to the patient without humidifying and/or heating the patient's surroundings. Room-based systems (e.g. a sauna, an air conditioner, an evaporative cooler), for example, may also humidify air that is breathed in by the patient, however they would also humidify and/or heat the entire room, which may cause discomfort to the occupants.

The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

Respiratory humidifiers are available in many forms and may be a standalone device that is coupled to an RPT device via an air circuit, is integrated with the RPT device or configured to be directly coupled to the relevant RPT device. While known passive humidifiers can provide some relief, generally a heated humidifier may be used to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, a gas inlet to receive gas from the flow generator or RPT device, and a gas outlet adapted to be connected to an air circuit that delivers the humidified gas to the patient interface.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

One form of the present technology comprises a patient interface for delivery of a flow of air into one or more nares of a patient, the patient interface comprising a plenum chamber configured to receive a flow of air; a prong for delivering the flow of air from the plenum chamber into a naris of the patient; and a frame coupled to the plenum chamber, the frame adapted to engage a head of the patient in use for locating the plenum chamber with respect to the naris of the patient, wherein a portion of the frame is recessed from at least a portion of the plenum chamber in an anterior direction to allow the portion of the plenum chamber to be displaced in the anterior direction into the recess.

According to one form of the present technology, the portion of the frame is recessed from a central portion of the plenum chamber.

According to one form of the present technology, the portion of the frame is rigidly configured.

According to one form of the present technology, the central portion of the plenum chamber is configured to engage an upper lip of the patient in use.

According to one form of the present technology, the plenum chamber is substantially tubular.

According to one form of the present technology, the plenum chamber is oriented in a direction substantially normal to the sagittal plane in use.

According to one form of the present technology, the frame engages a first end and a second end of the plenum chamber.

According to one form of the present technology, the plenum chamber comprises an opening configured to connect to an air circuit for receiving the flow of air.

According to one form of the present technology, the plenum chamber comprises an elastic, flexible material.

According to one form of the present technology, the prong extends outwardly from the plenum chamber toward the naris of the patient.

According to one form of the present technology, the prong is configured to be inserted into the naris of the patient.

According to one form of the present technology, the prong is integrally formed with the plenum chamber.

According to one form of the present technology, the prong extends in the superior and posterior direction towards the patient.

According to one form of the present technology, the prongs are curved.

According to one form of the present technology, the frame comprises a rigid portion adapted to engage a face of the patient in use.

According to one form of the present technology, the rigid portion is adapted to engage a maxilla of the patient in use.

One form of the present technology, further comprises a headgear coupled to the frame.

According to one form of the present technology, the headgear is elastic.

According to one form of the present technology, the headgear comprises a top strap and a rear strap.

According to one form of the present technology, the headgear is bifurcated.

One form of the present technology comprises a patient interface for delivering a flow of air to an entrance of a patient's airways, the patient interface comprising a plenum chamber configured to receive a flow of air; one or more prongs configured to deliver the flow of air from the plenum chamber to the entrance of a patient's airways; a rigid frame configured to engage a cheek of the patient in use; and a headgear coupled to the rigid frame and configured to engage with the patient's head to locate the one or more prongs in use, wherein the rigid frame comprises a central portion that are disengaged from and extends past the plenum chamber in the anterior and posterior direction.

According to one form of the present technology, the central portion comprises a plurality of strut members.

According to one form of the present technology, the plurality of strut members are joined at an angle.

According to one form of the present technology, the plurality of strut members form a triangulated structure.

According to one form of the present technology, the portion of the frame substantially extends across the width of the plenum chamber.

According to one form of the present technology, locations of engagement between the central portion and the plenum chamber consists of a left end and a right end of the plenum chamber.

According to one form of the present technology, the central portion comprises acurve.

According to one form of the present technology, the central portion is curved across a width of the plenum chamber.

According to one form of the present technology, the plenum chamber has a negligible effect to the rigidity of the patient interface.

One form of the present technology comprises two prongs.

According to one form of the present technology, the plenum chamber is cylindrically shaped.

According to one form of the present technology, the plenum chamber is a substantially straight cylinder.

According to one form of the present technology, the plenum chamber comprises silicone.

According to one form of the present technology, the plenum chamber and the one or more prongs are integrally formed.

According to one form of the present technology, the rigid frame comprises a left side portion and a right side portion.

According to one form of the present technology, the rigid frame is formed by moulding.

One form of the present technology, further comprises a headgear.

One form of the present technology relates to a respiratory therapy system, comprising: a respiratory therapy device configured to generate a flow of breathable gas; a humidifier configured to be coupled to the respiratory therapy device to humidify the flow of breathable gas; an air circuit to deliver the flow of breathable gas; and a patient interface according to the present technology.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of a nasal pillows, receives a supply of air at positive pressure from an RPT device 4000. Air from the RPT device is humidified in a humidifier 5000, and passes along an air circuit 4170 to the patient 1000. A bed partner 1100 is also shown.

4.2 Respiratory System and Facialanatomy

Figure 2A:
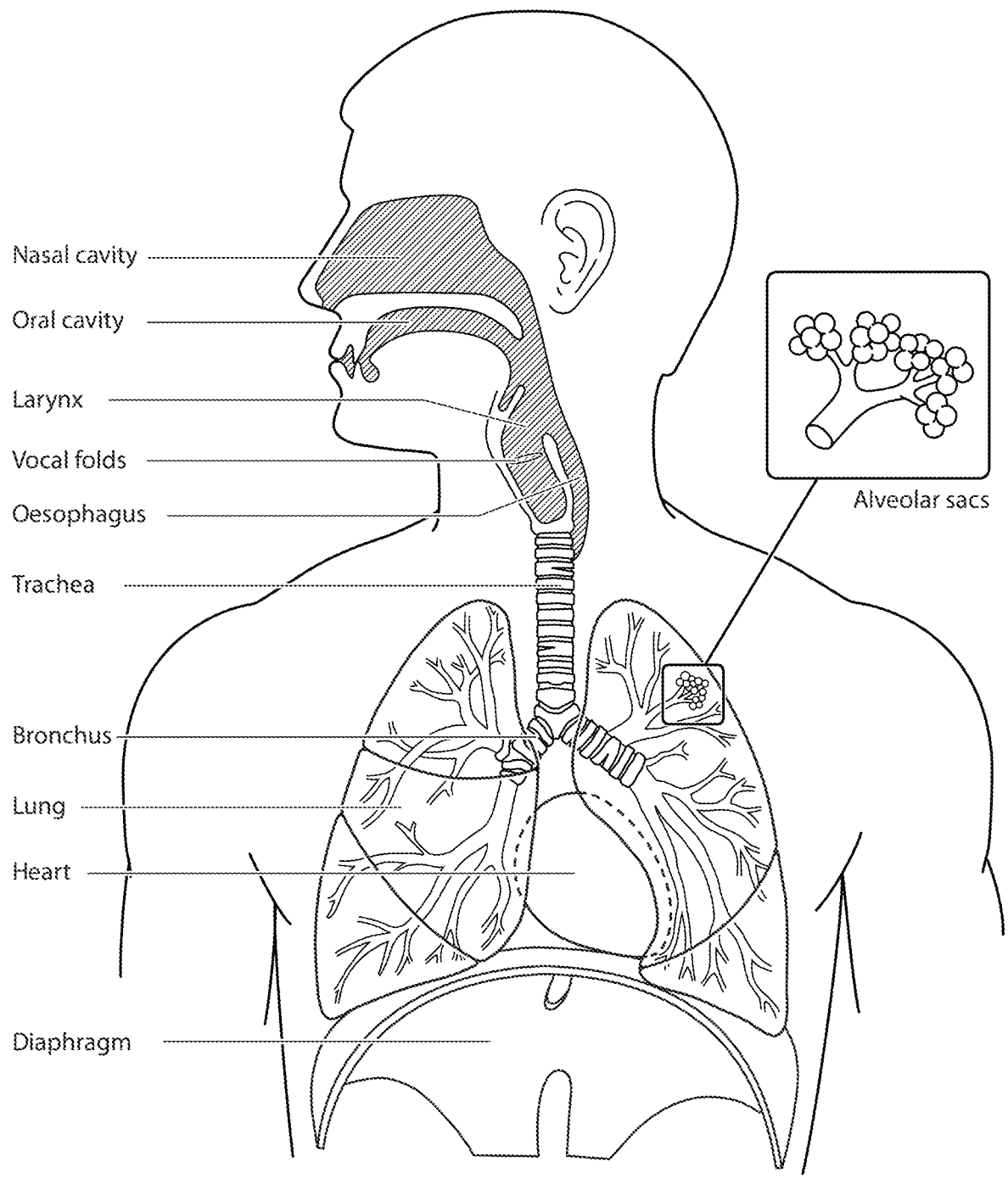

FIG. 2A shows an overview of a human respiratory system including the nasal and oral cavities, the larynx, vocal folds, oesophagus, trachea, bronchus, lung, alveolar sacs, heart and diaphragm.

Figure 2B:
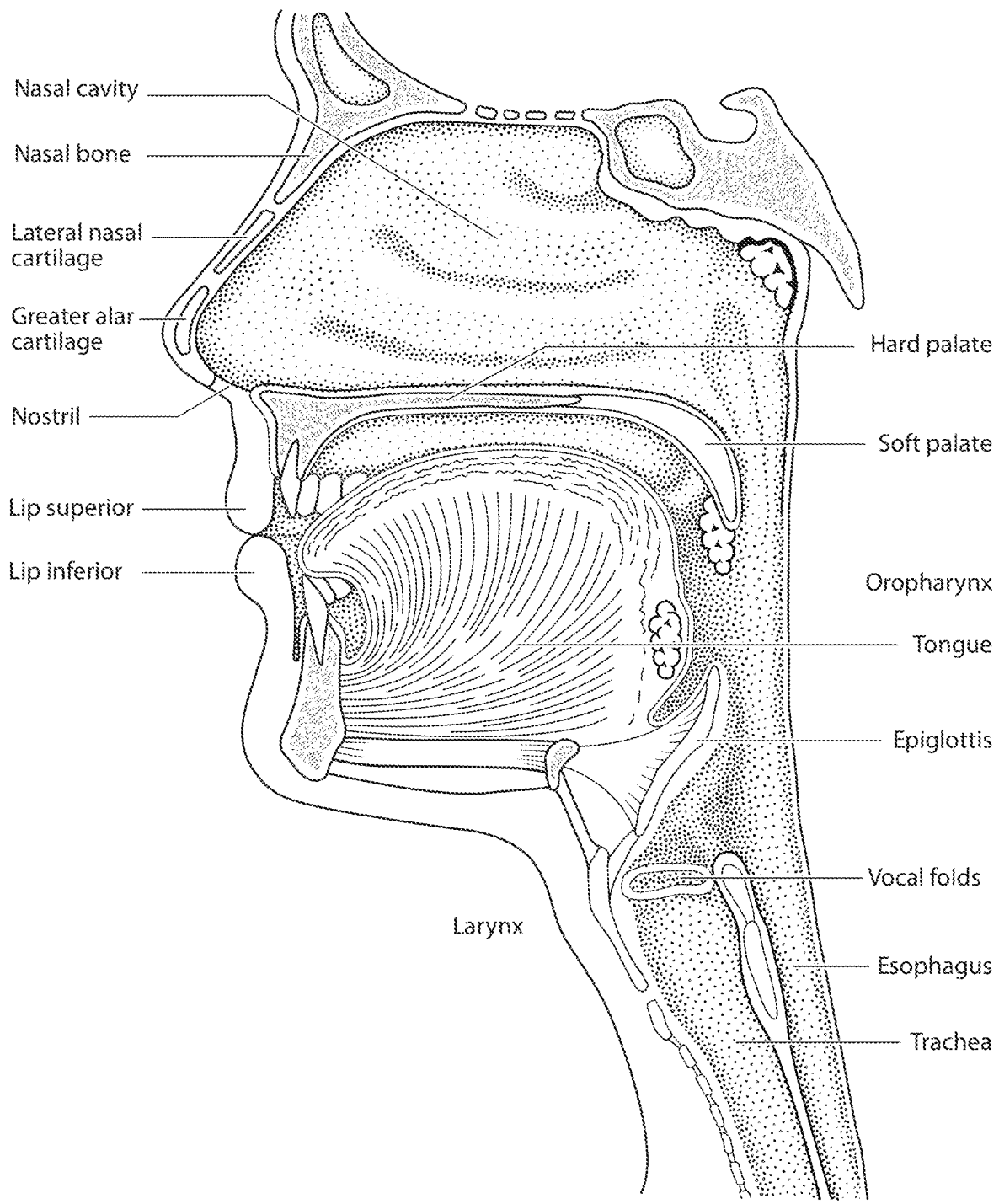

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
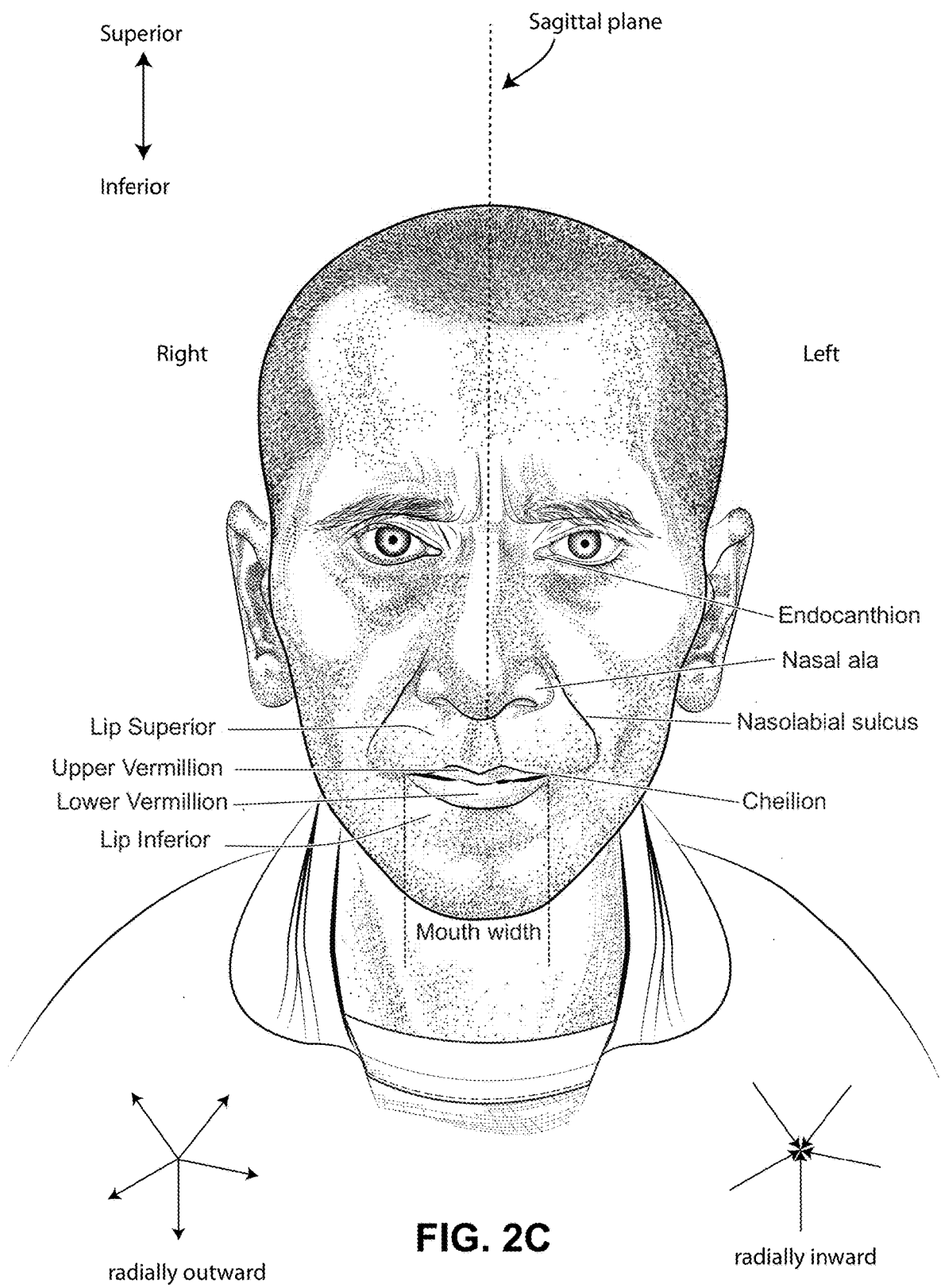

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
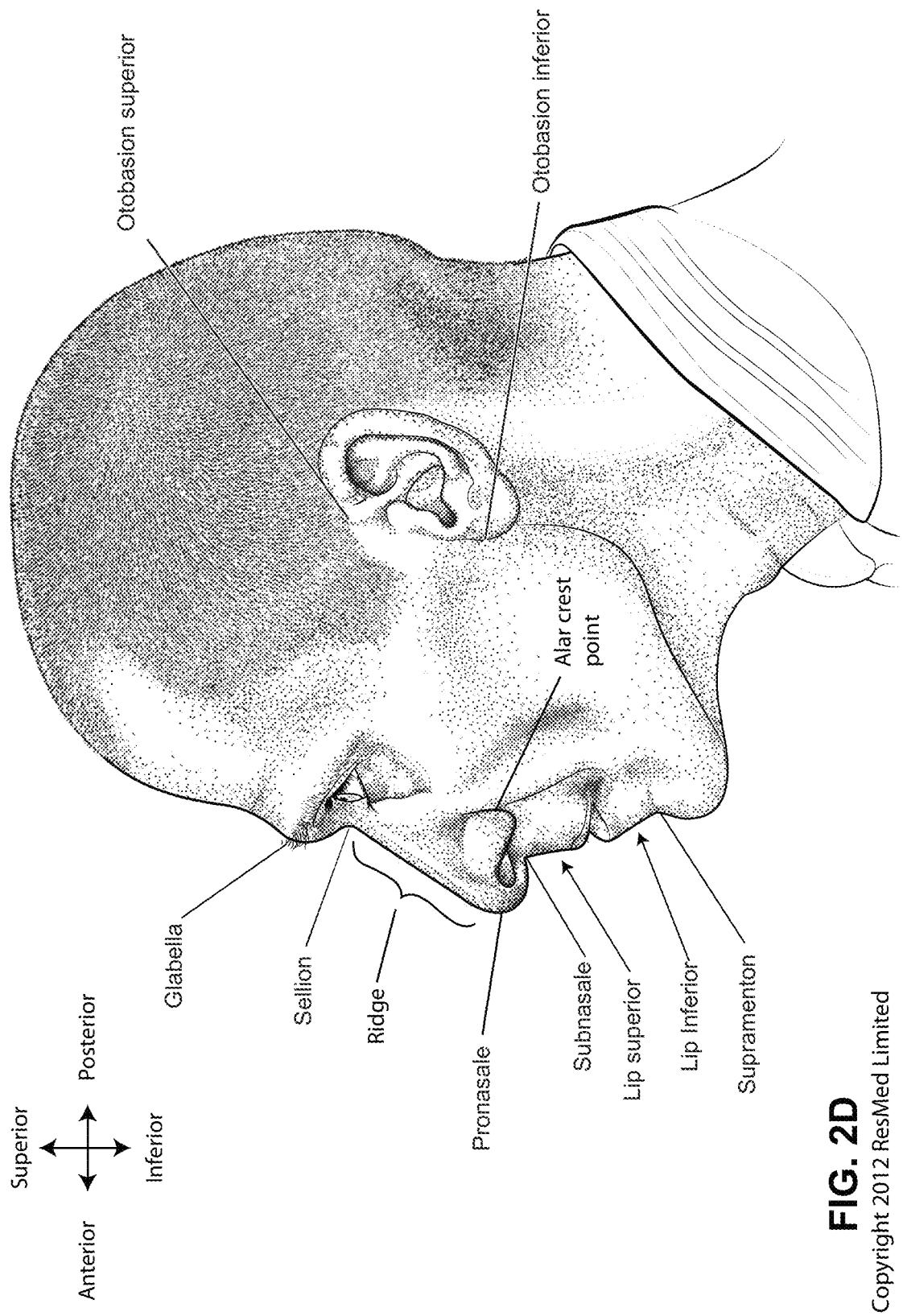

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
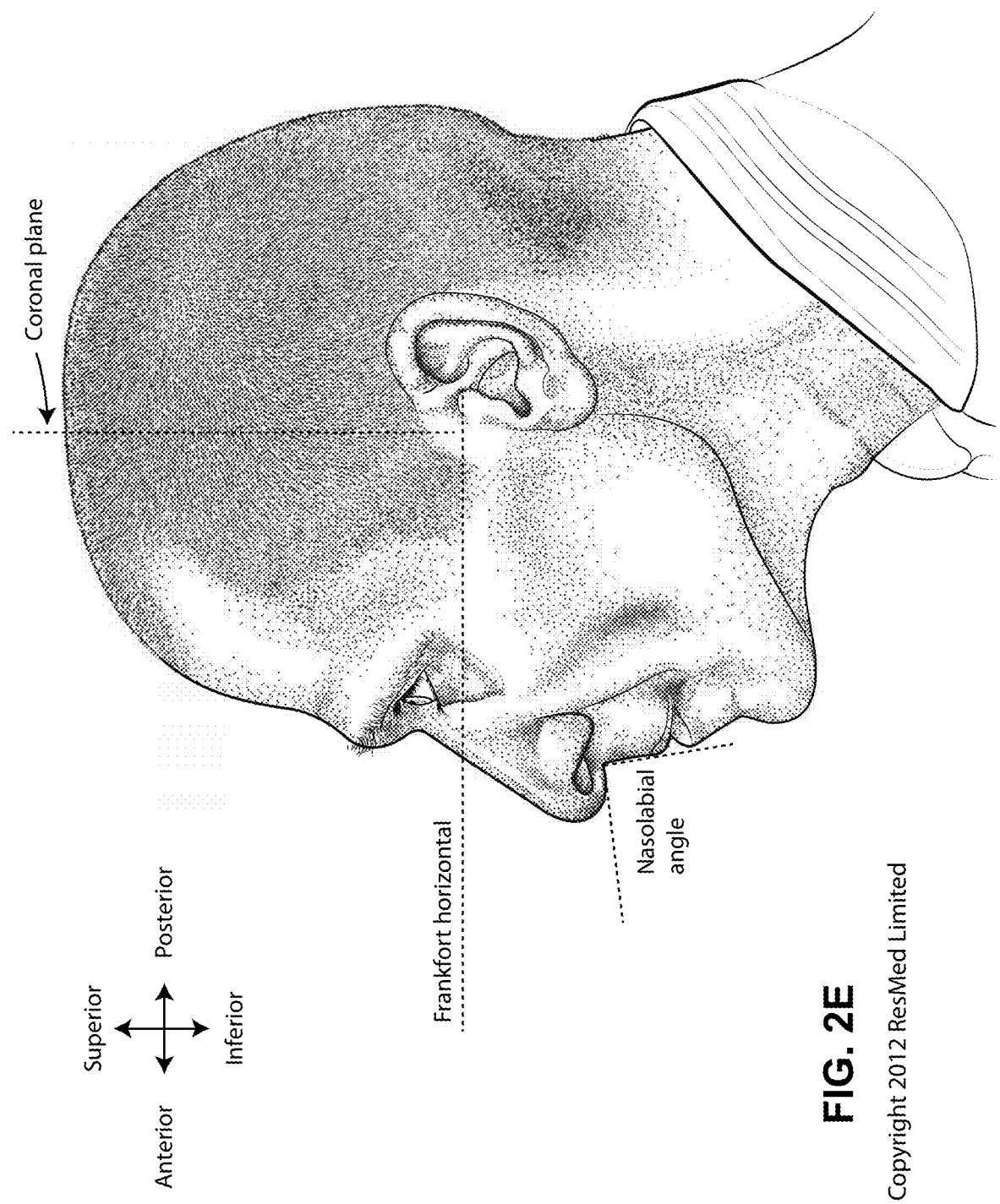

FIG. 2E is a further side view of a head. The approximate locations of the Frankfort horizontal and nasolabial angle are indicated. The coronal plane is also indicated.

Figure 2F:
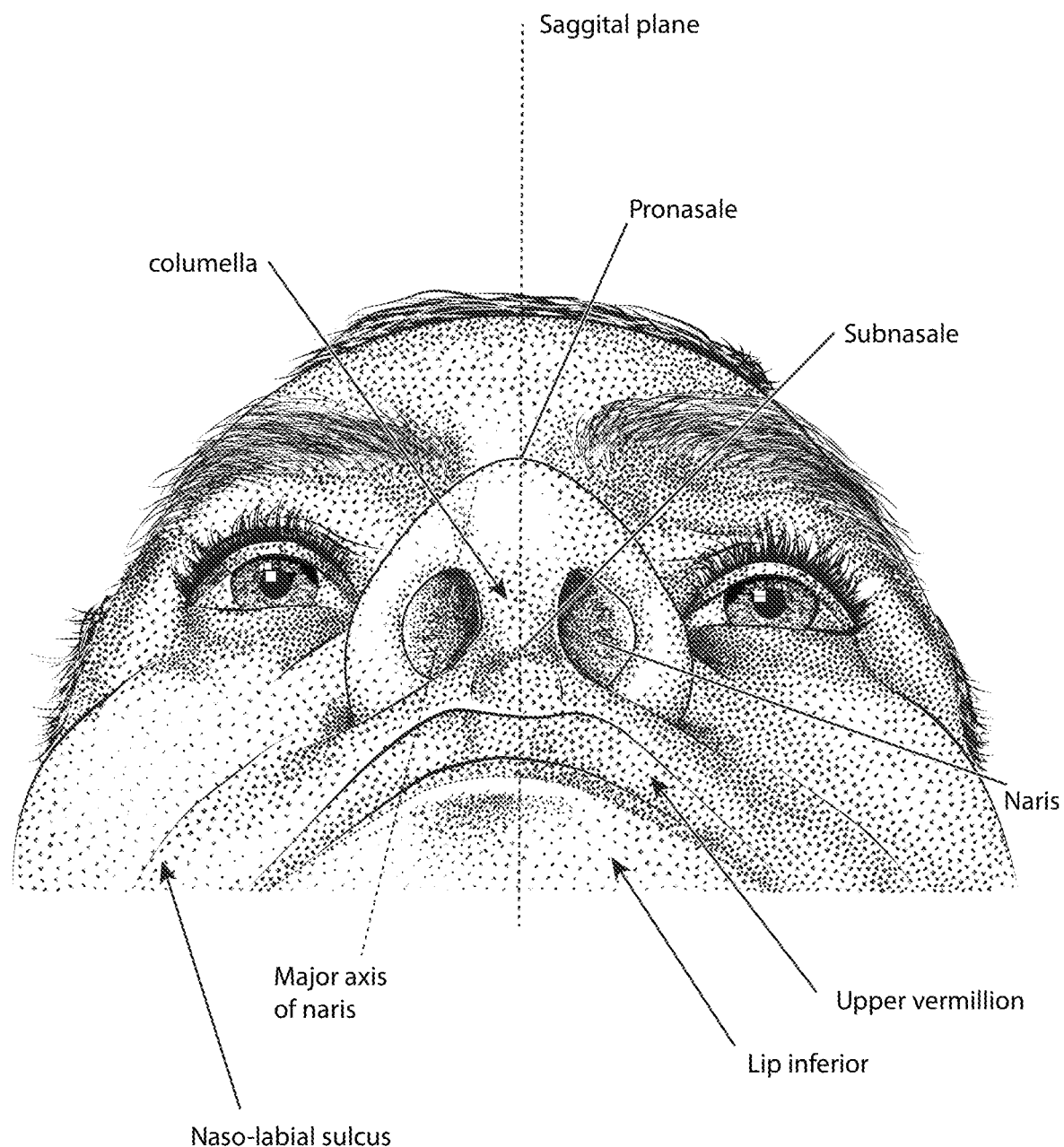

FIG. 2F shows a base view of a nose with several features identified including naso-labial sulcus, lip inferior, upper Vermilion, naris, subnasale, columella, pronasale, the major axis of a naris and the sagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

Figures 2J, 2K:
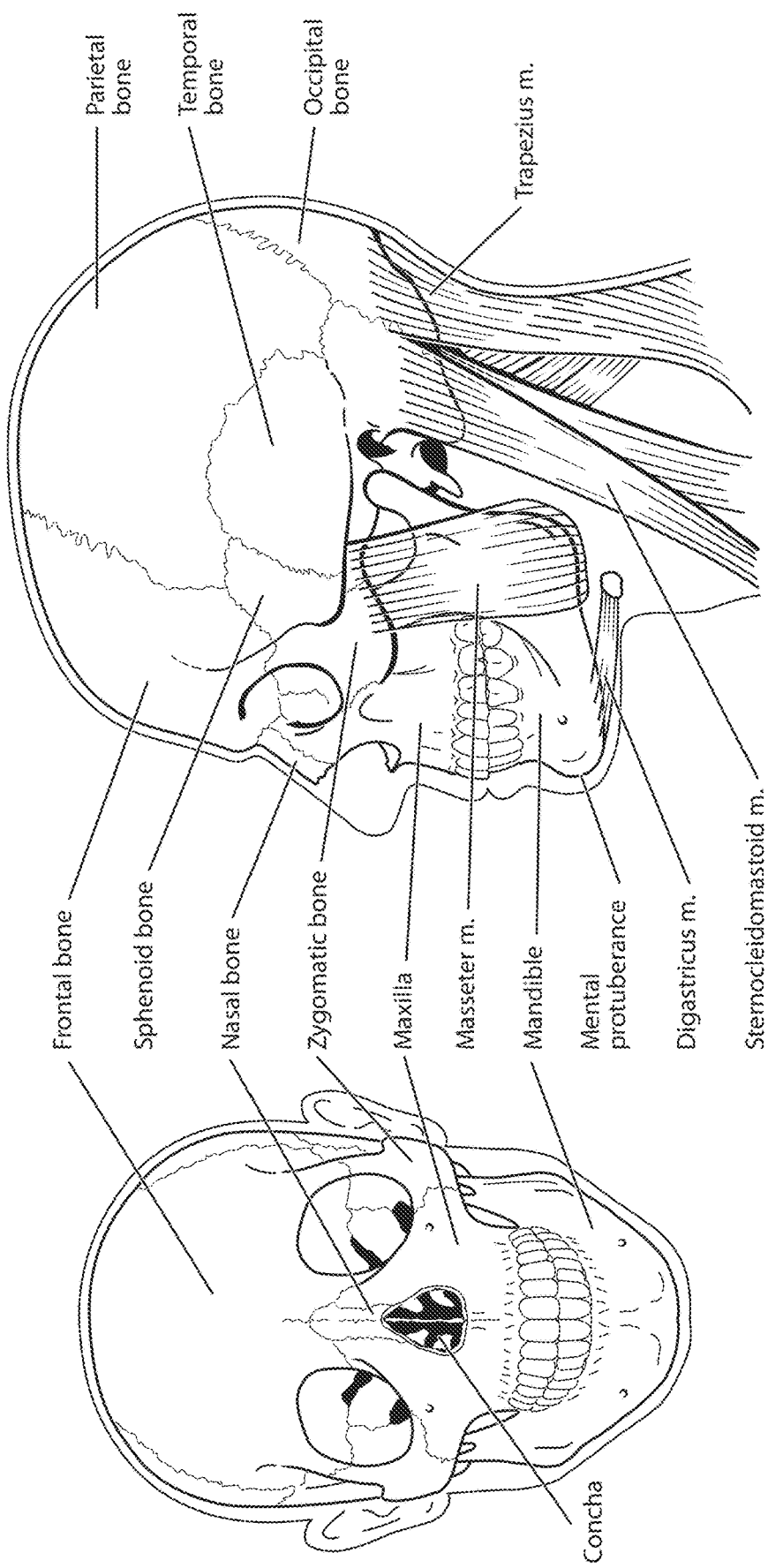

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
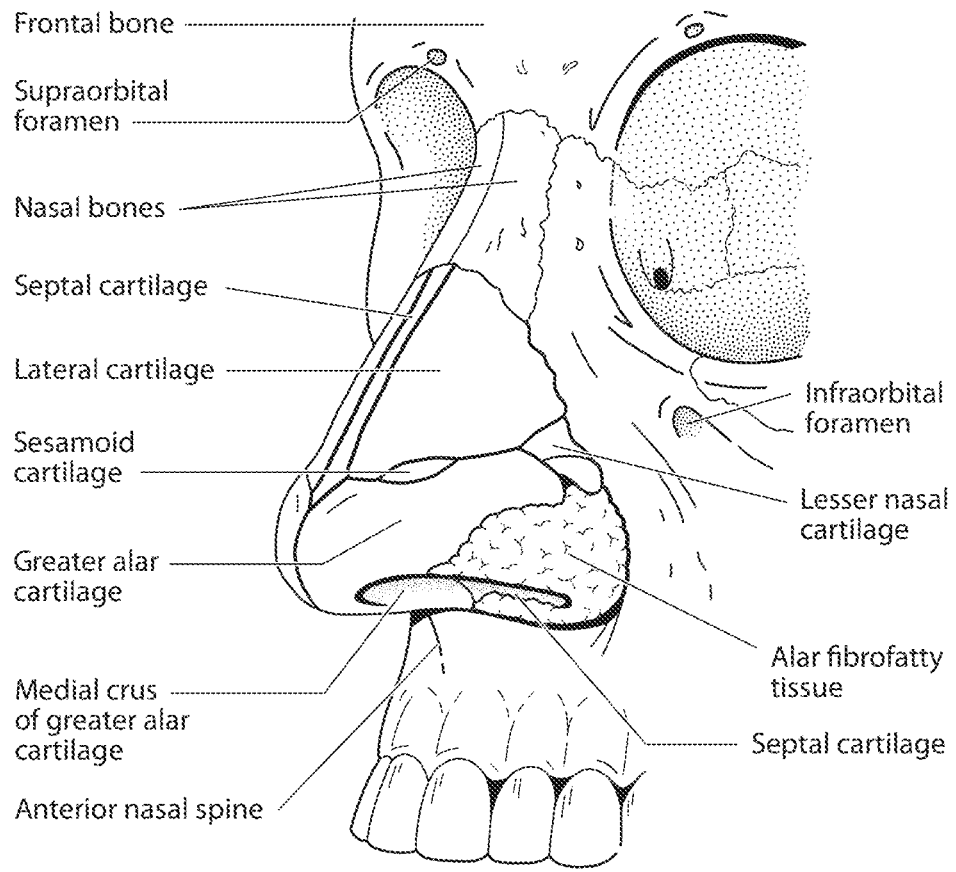

FIG. 2L shows an anterolateral view of a nose.

4.3 Patient Interface

Figure 3A:
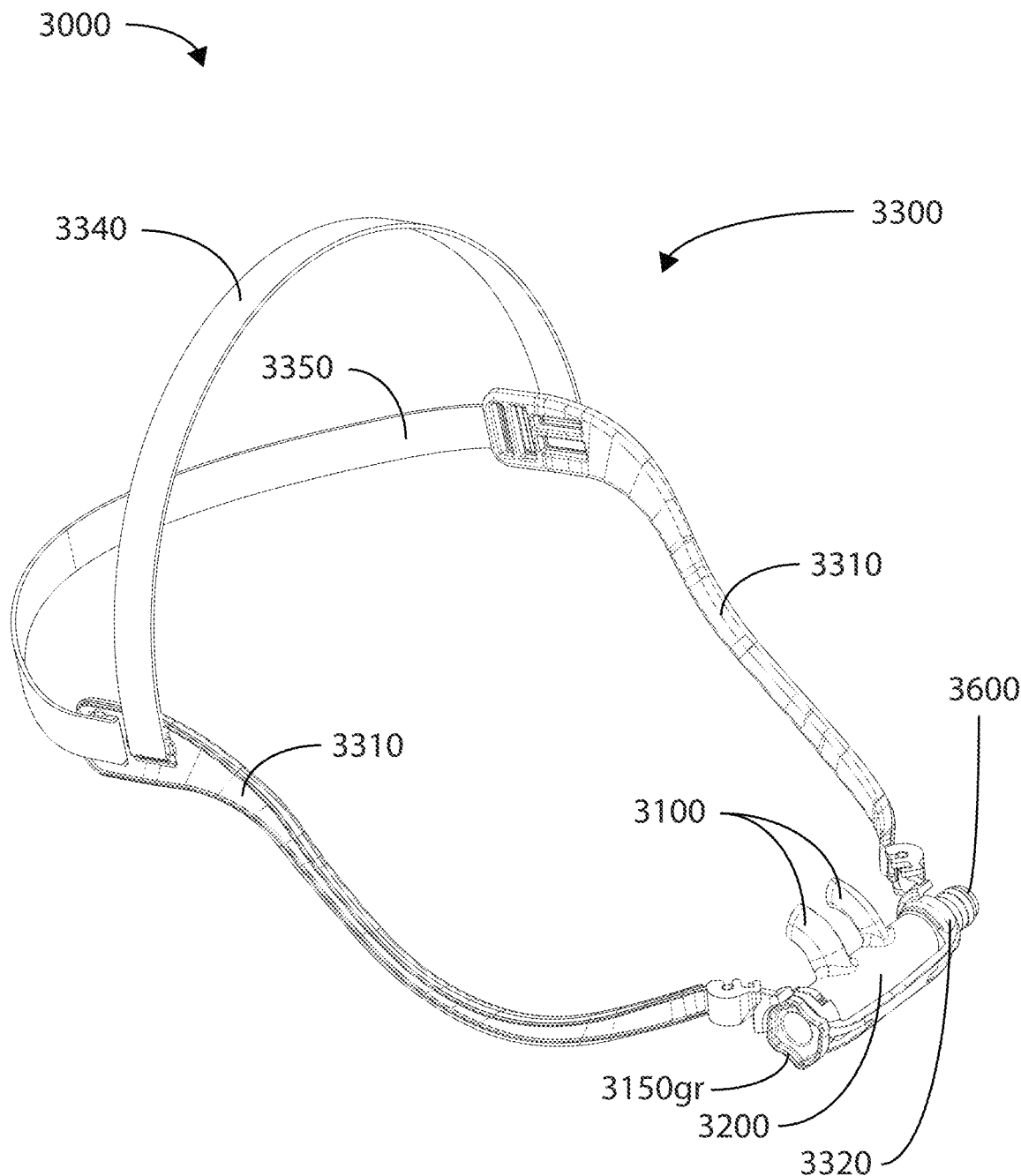

FIG. 3A shows a side perspective view of a patient interface in the form of a nasal cannula in accordance with one form of the present technology.

Figure 3B:
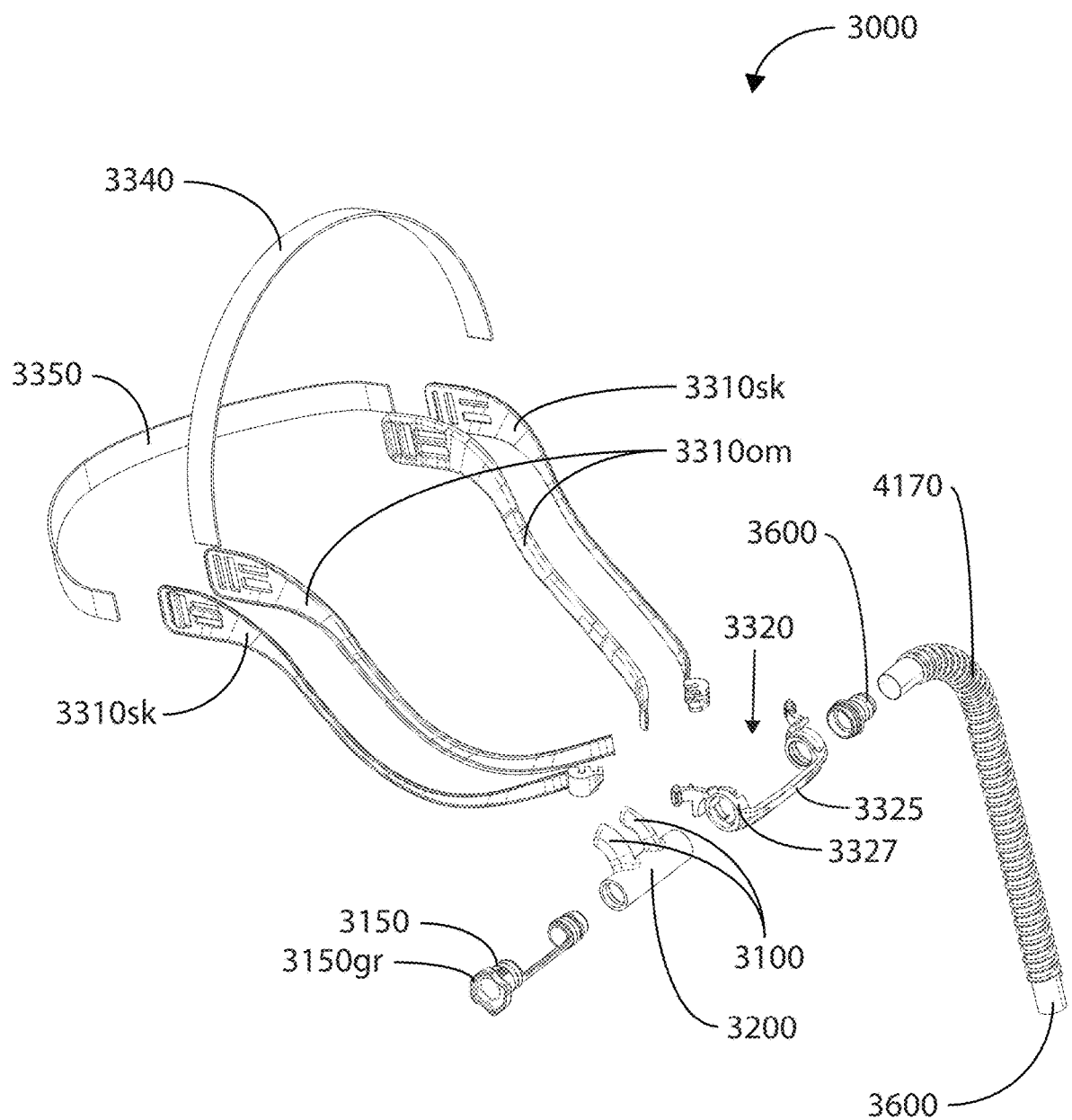

FIG. 3B shows an exploded side perspective view of a patient interface and an air circuit in the form of a nasal cannula in accordance with one form of the present technology.

Figure 3C:
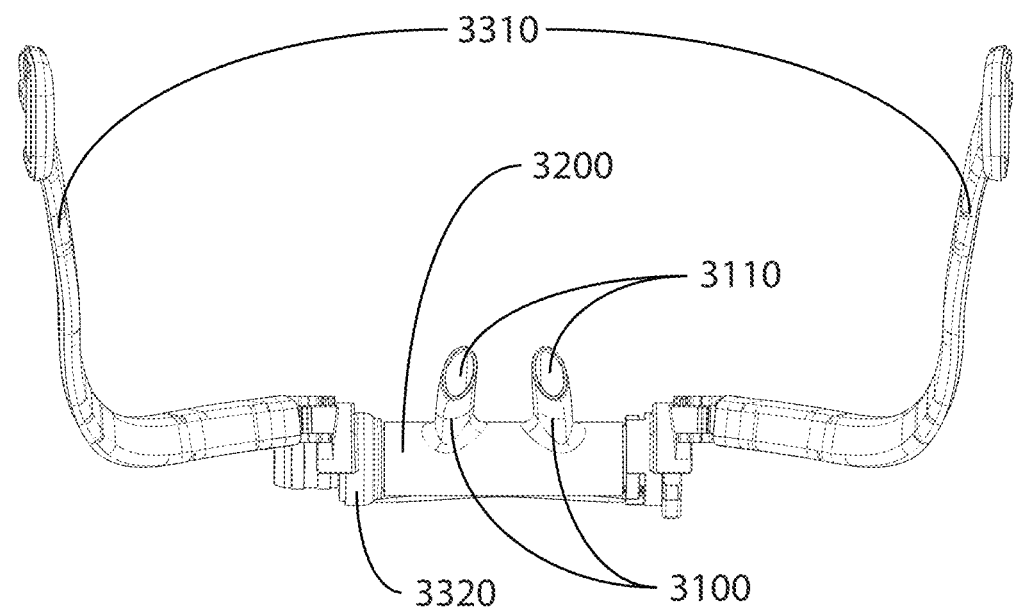

FIG. 3C shows a rear view of a patient interface in the form of a nasal cannula in accordance with one form of the present technology.

Figure 3D:
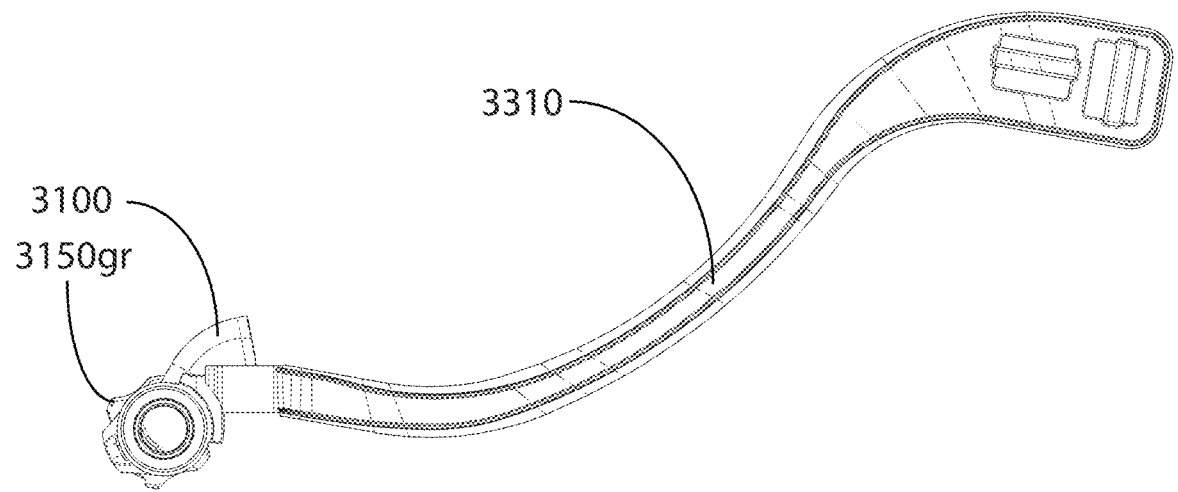

FIG. 3D shows a side view of a patient interface in the form of a nasal cannula in accordance with one form of the present technology.

Figure 3E:
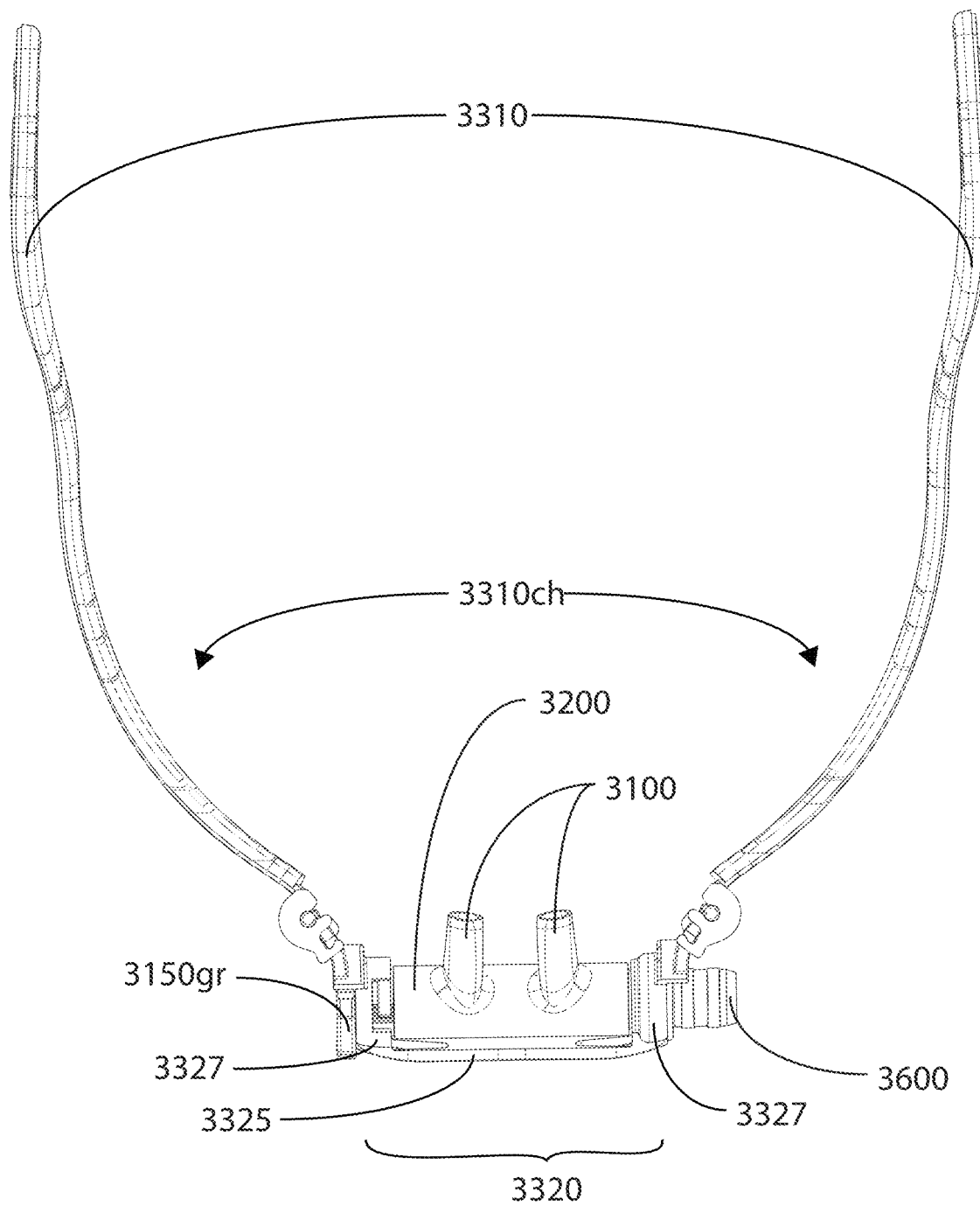

FIG. 3E shows a top view of a patient interface in the form of a nasal cannula in accordance with one form of the present technology.

Figure 3F:
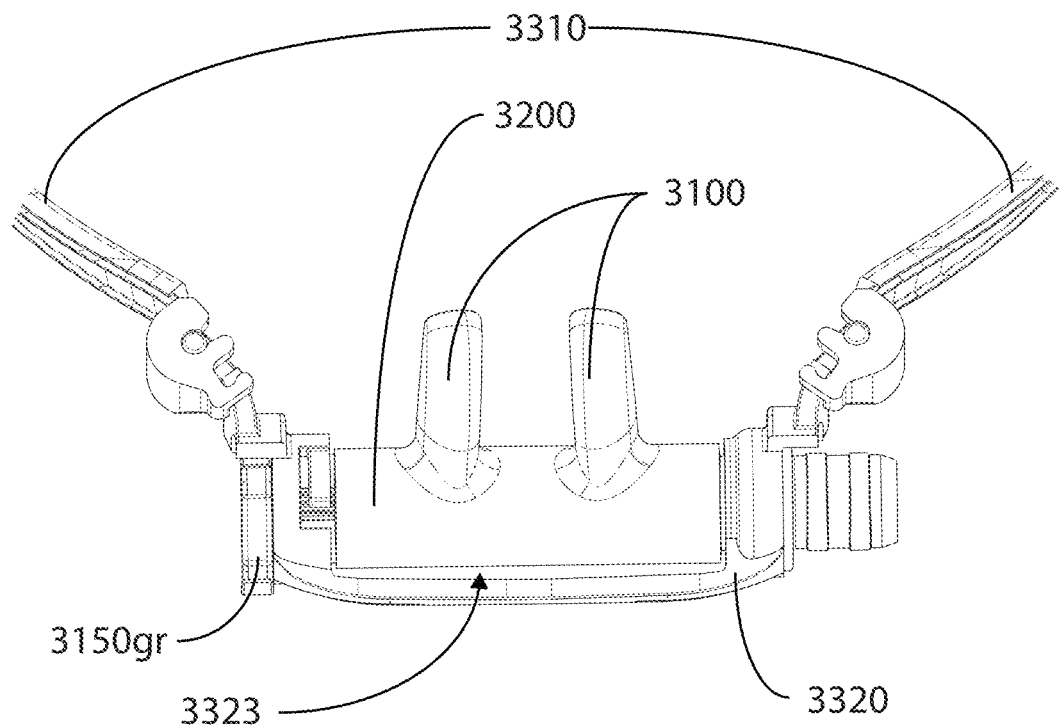

FIG. 3F shows a top view of a portion of a patient interface in the form of a nasal cannula in accordance with one form of the present technology.

Figure 3G:
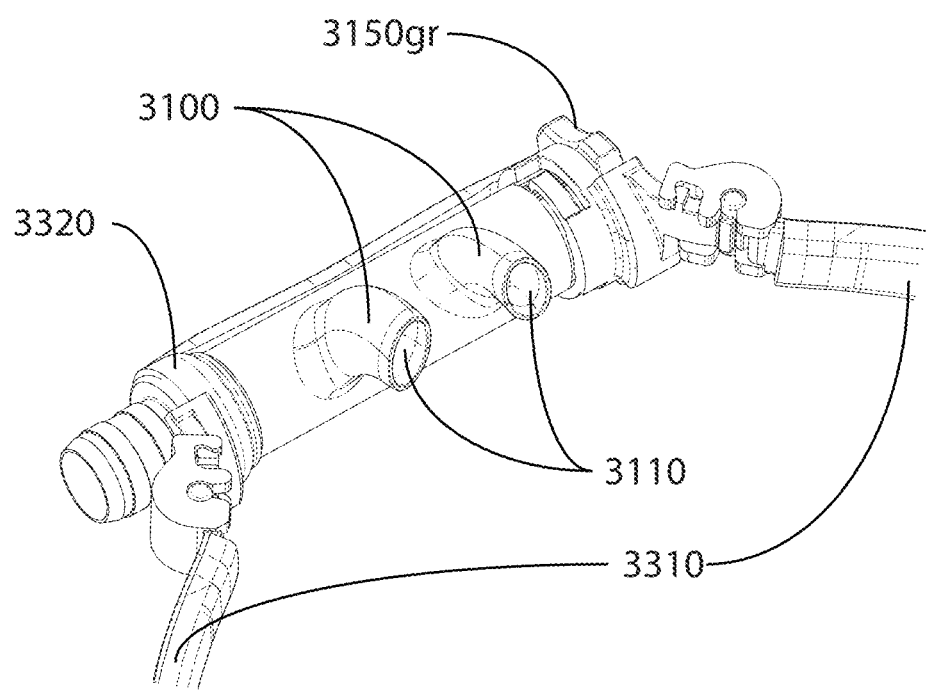

FIG. 3G shows a rear perspective view of a portion of a patient interface in the form of a nasal cannula in accordance with one form of the present technology.

Figure 3H:
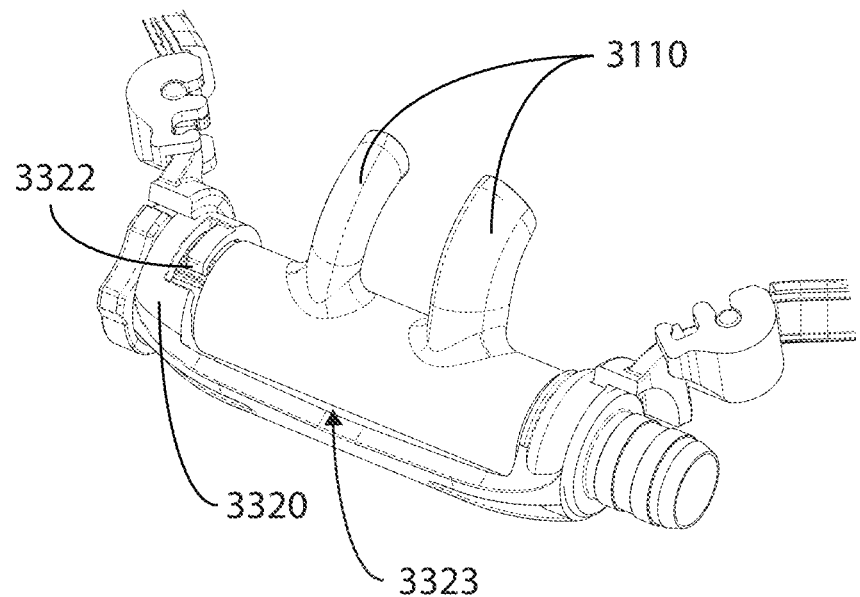

FIG. 3H shows a front perspective view of a portion of a patient interface in the form of a nasal cannula in accordance with one form of the present technology.

Figure 3I:
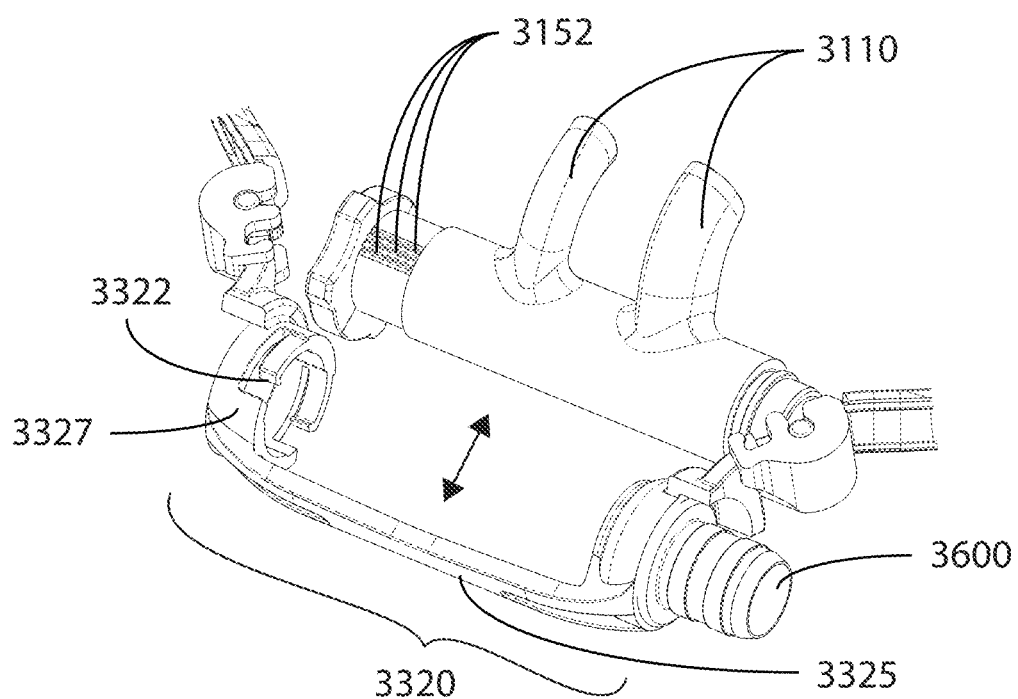

FIG. 3I shows a front perspective view of a portion of a patient interface in the form of a nasal cannula in accordance with one form of the present technology, wherein the nasal prongs, the manifold and the barrel are shown exploded from the cannula frame.

Figure 3J:
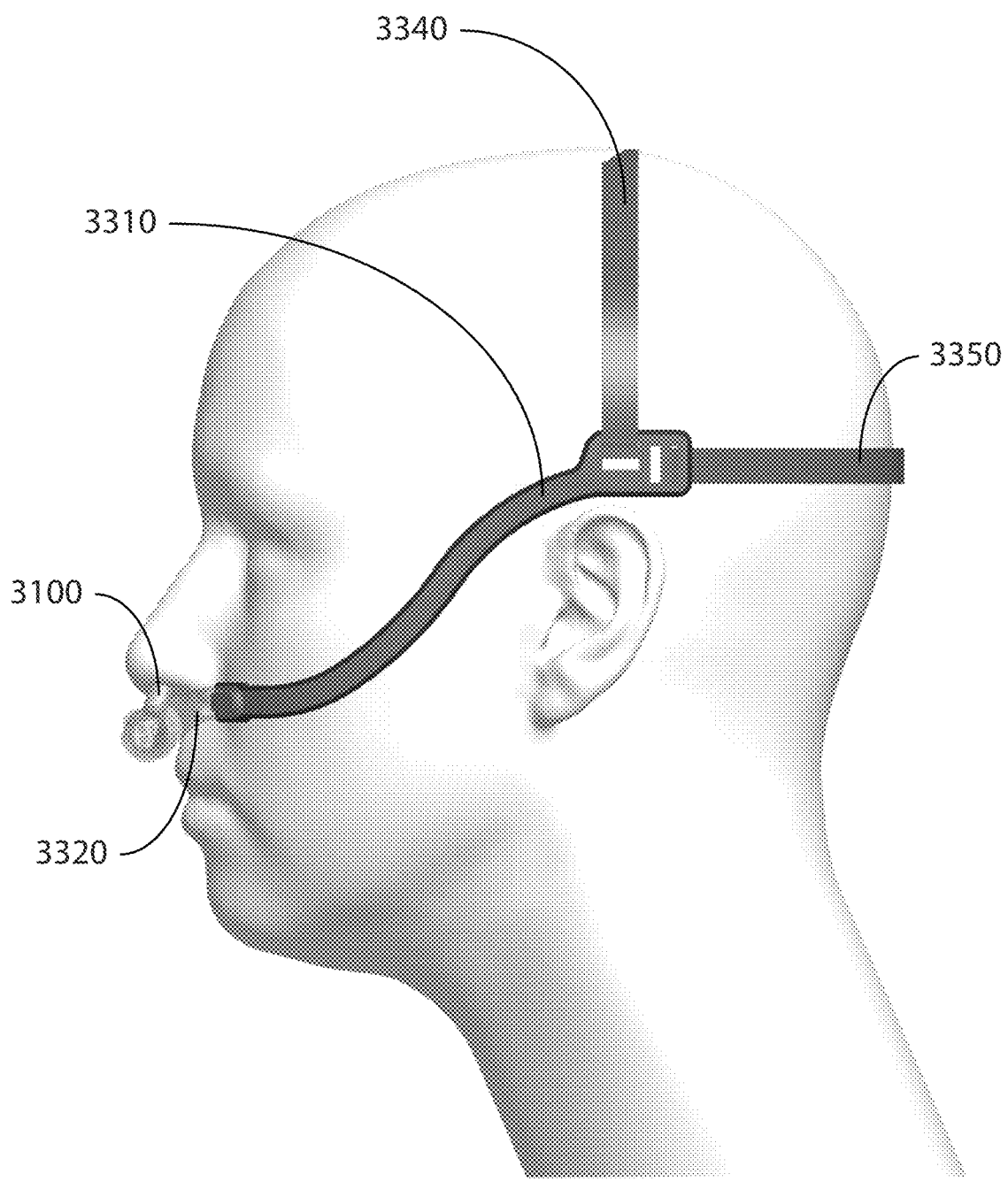

FIG. 3J shows a side view of a patient interface in the form of a nasal cannula in accordance with one form of the present technology, in an exemplary operating location and orientation on a head of a patient.

Figure 3K:
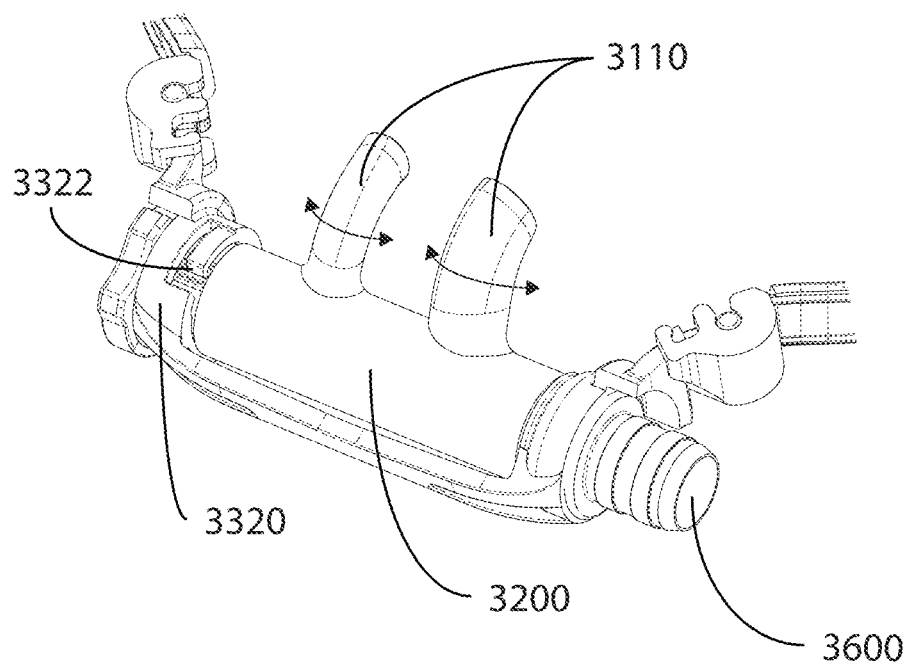

FIG. 3K shows a front perspective view of a portion of a patient interface in the form of a nasal cannula in accordance with one form of the present technology.

Figure 4A:
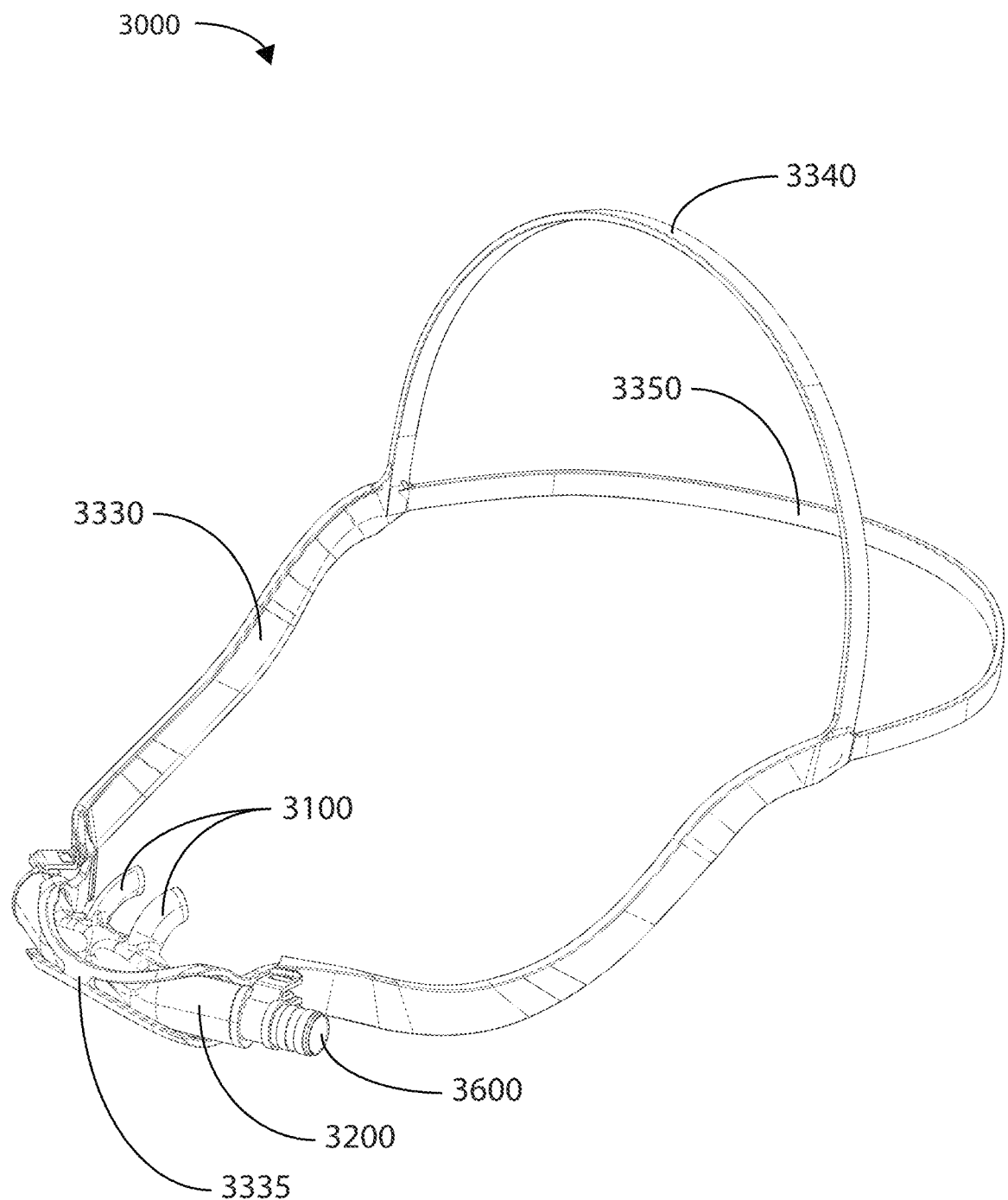

FIG. 4A shows a side perspective view of a patient interface in the form of a nasal cannula in accordance with one form of the present technology.

Figure 4B:
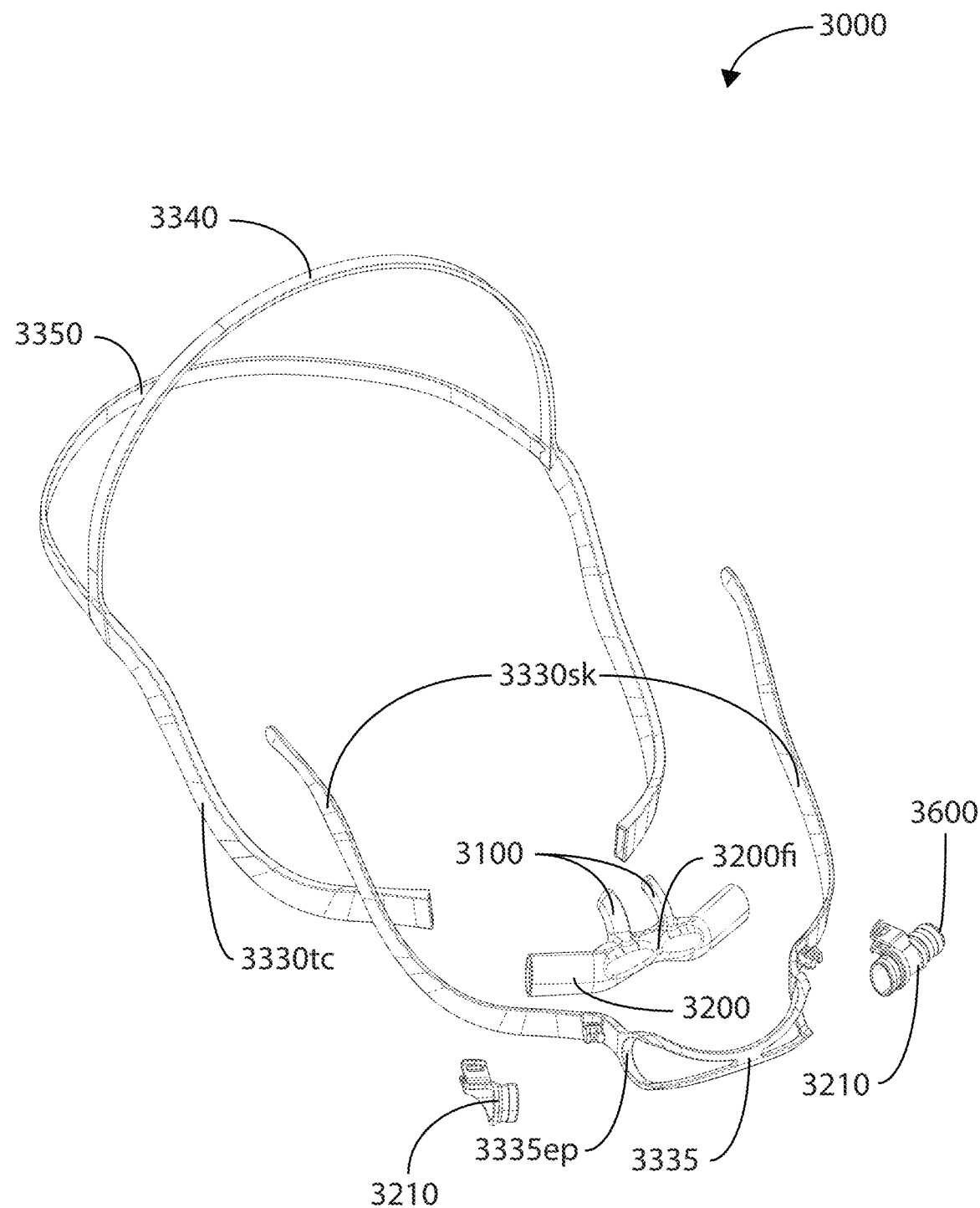

FIG. 4B shows an exploded side perspective view of a patient interface and an air circuit in the form of a nasal cannula in accordance with one form of the present technology.

Figure 4C:
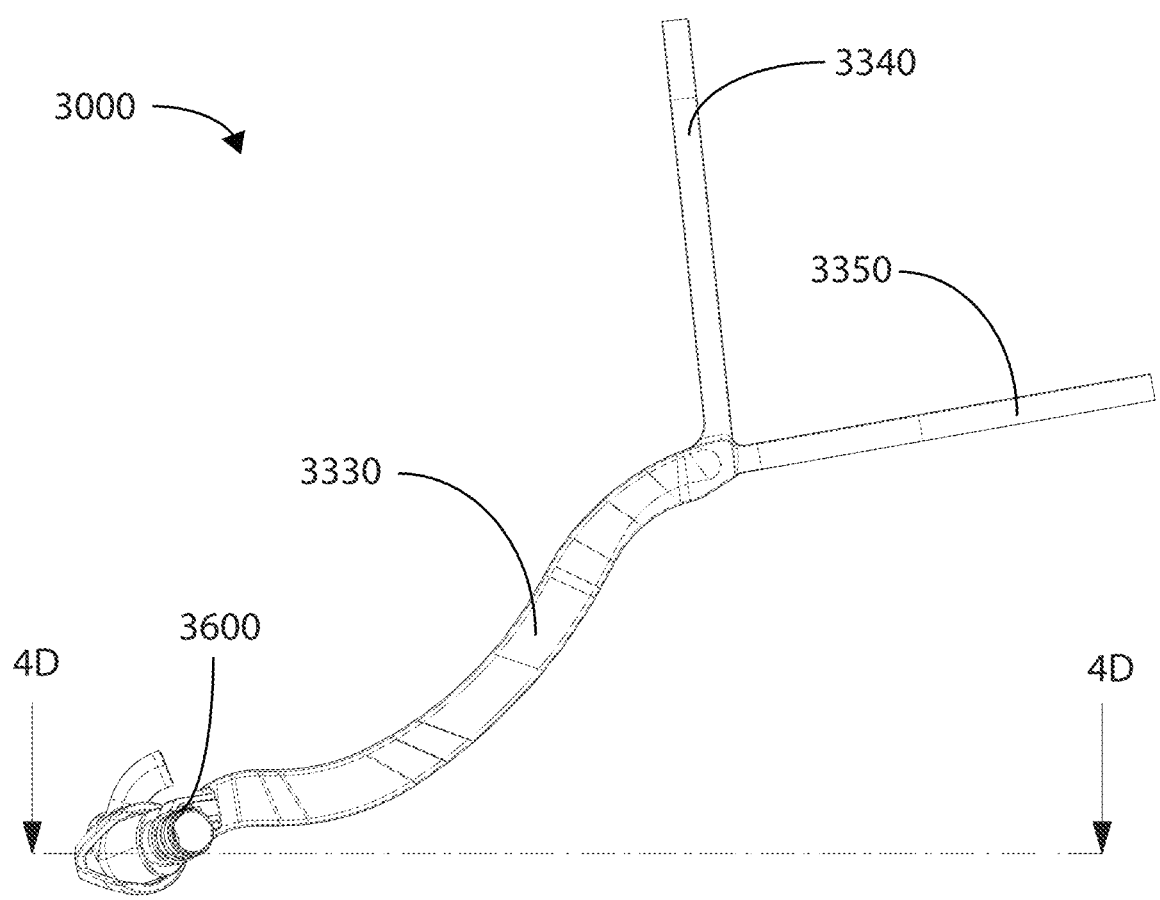
Figure 4D:
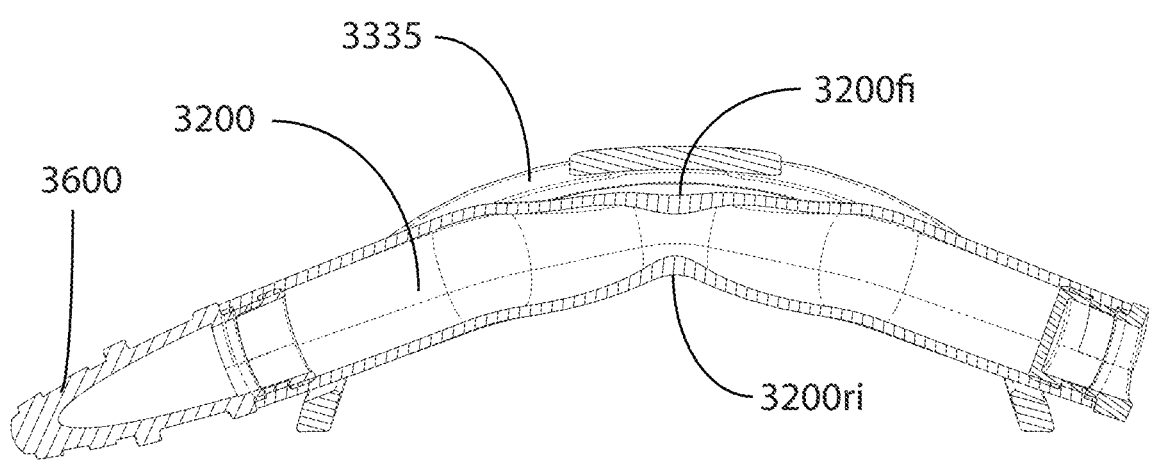

FIG. 4C shows a side view of a patient interface in the form of a nasal cannula in accordance with one form of the present technology, indicating a cross section as shown in FIG. 4D.

FIG. 4D shows a top view of a patient interface in the form of a nasal cannula in accordance with one form of the present technology, showing a cross section as indicated in FIG. 4C.

Figure 4E:
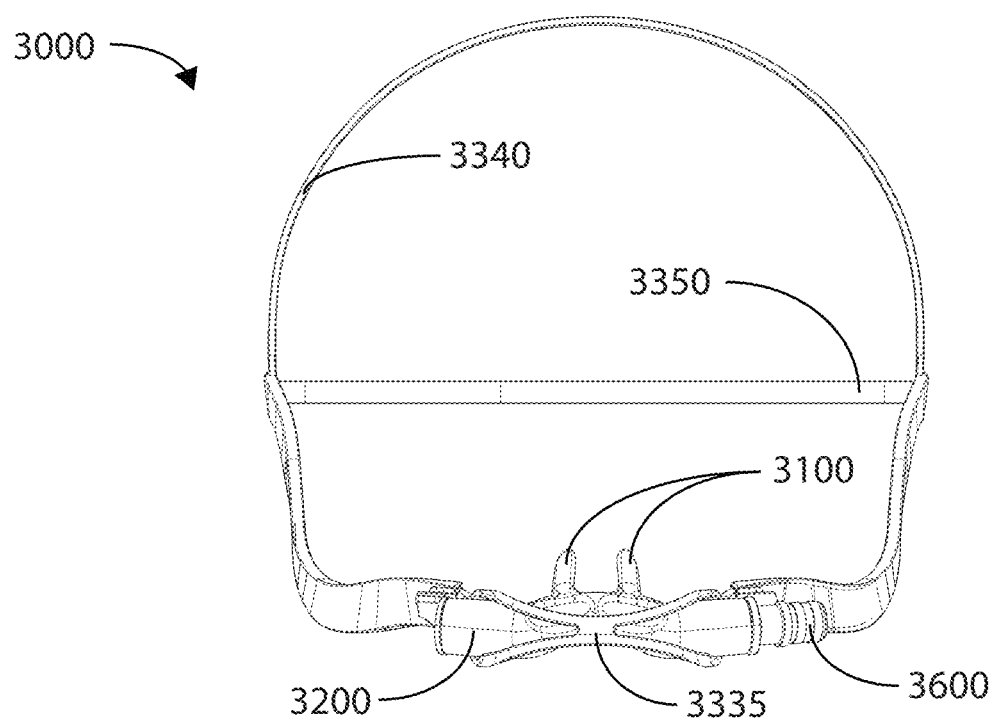

FIG. 4E shows a front view of a patient interface in the form of a nasal cannula in accordance with one form of the present technology.

Figure 4F:
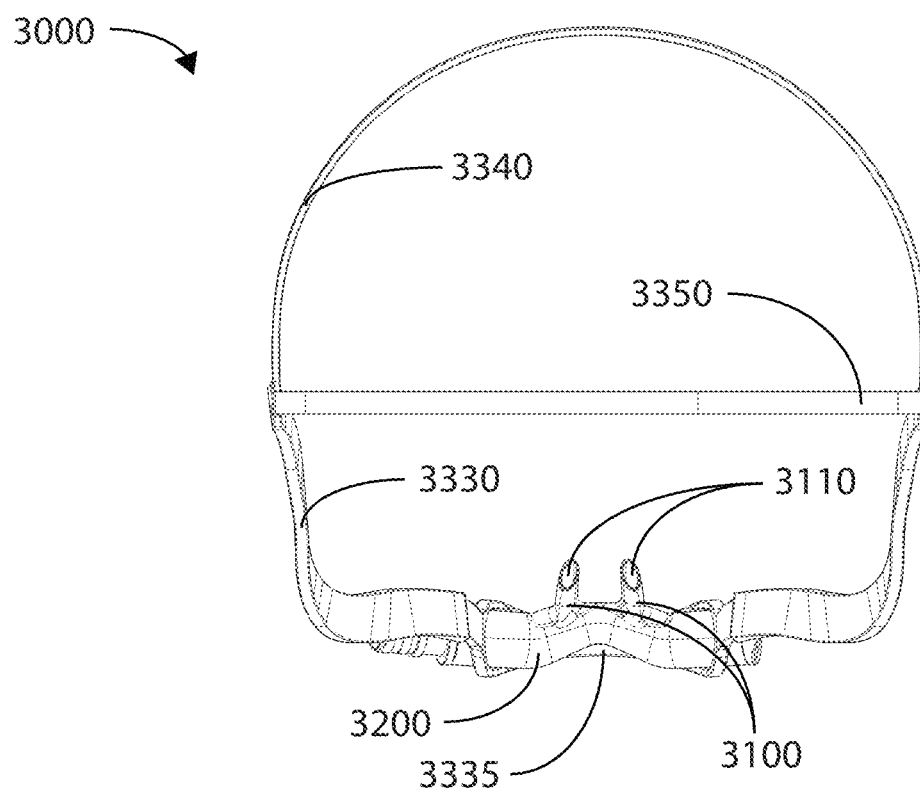

FIG. 4F shows a rear view of a patient interface in the form of a nasal cannula in accordance with one form of the present technology.

Figure 4G:
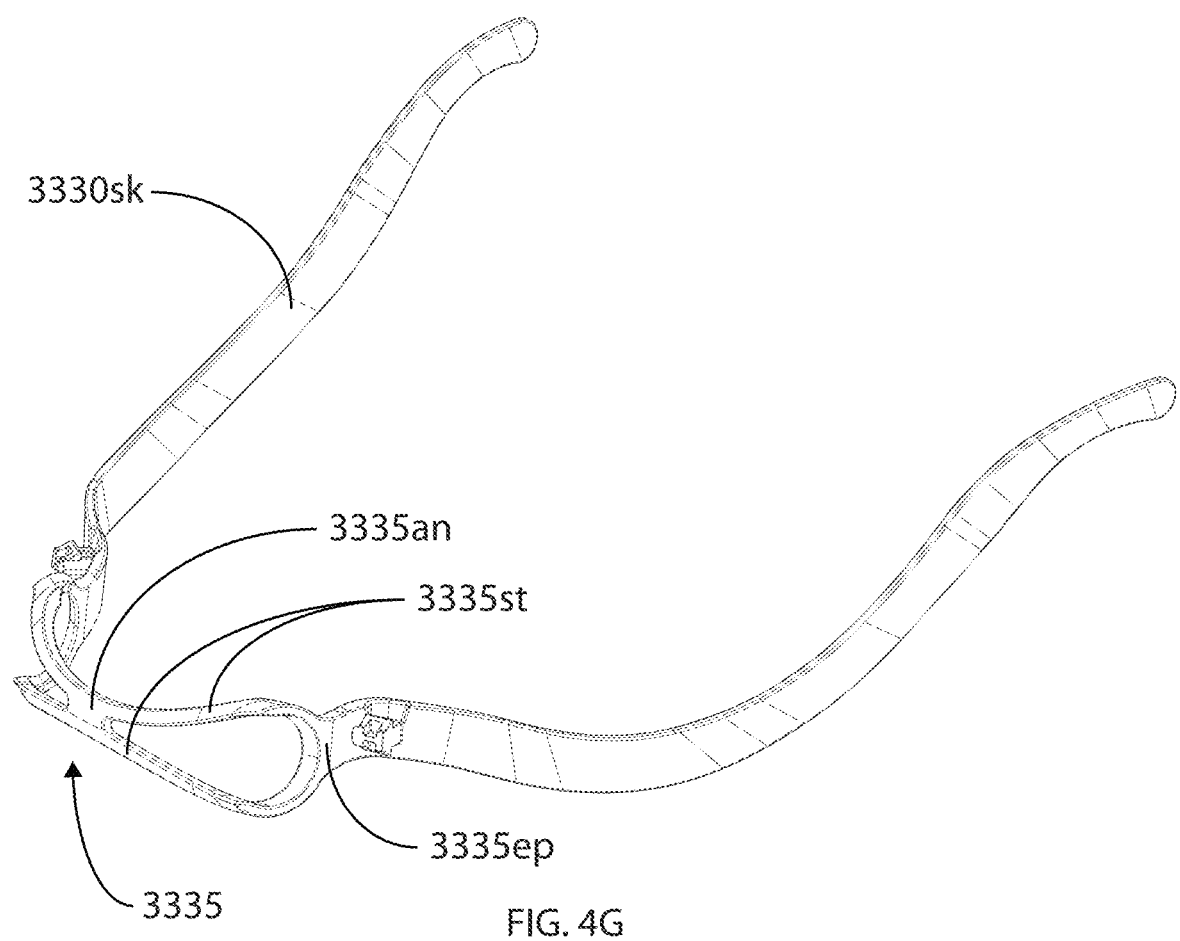

FIG. 4G shows a side perspective view of a frame of the patient interface in the form of a nasal cannula in accordance with one form of the present technology.

Figure 4H:
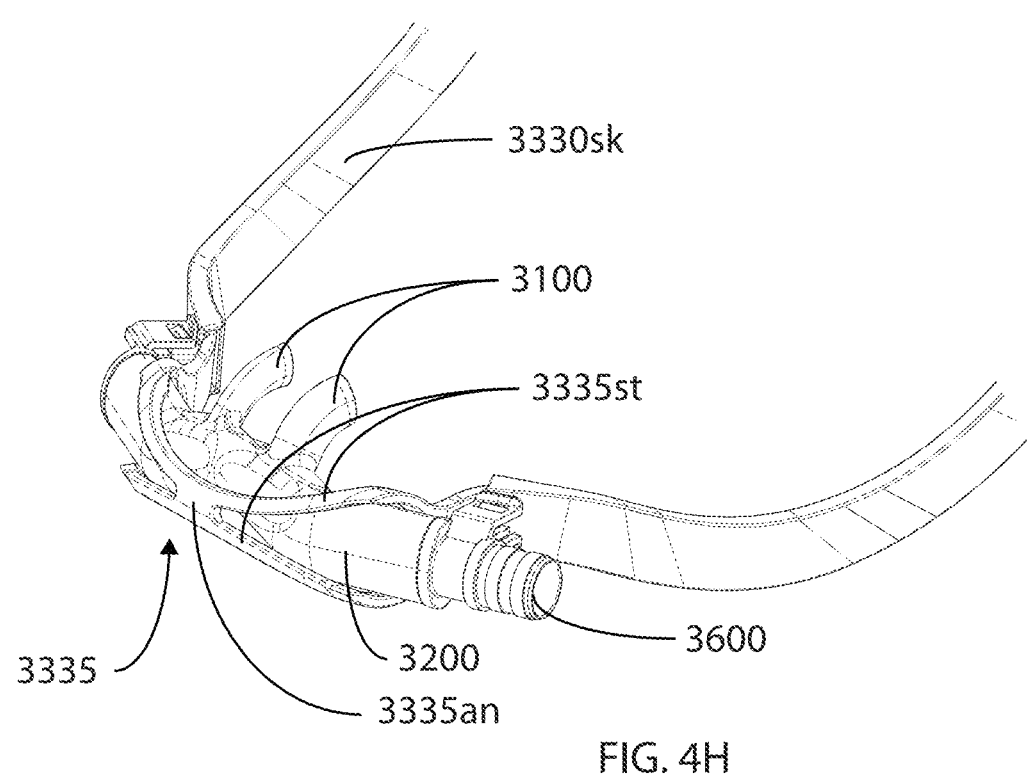

FIG. 4H shows a side perspective view of a frame of the patient interface in the form of a nasal cannula in accordance with one form of the present technology.

Figure 4I:
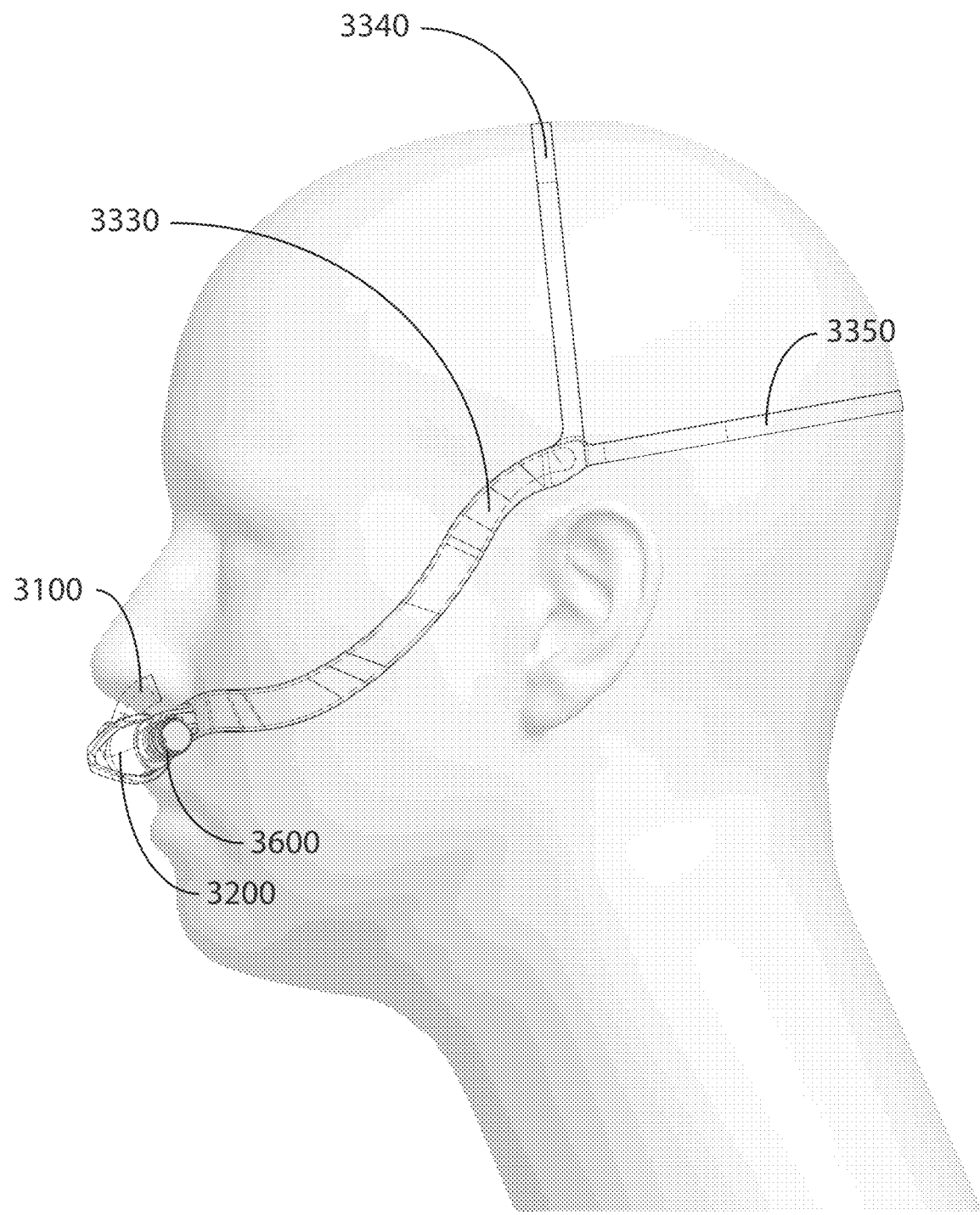

FIG. 4I shows a side view of a patient interface in the form of a nasal cannula in accordance with one form of the present technology as it may be placed on a head of a patient.

Figure 4J:
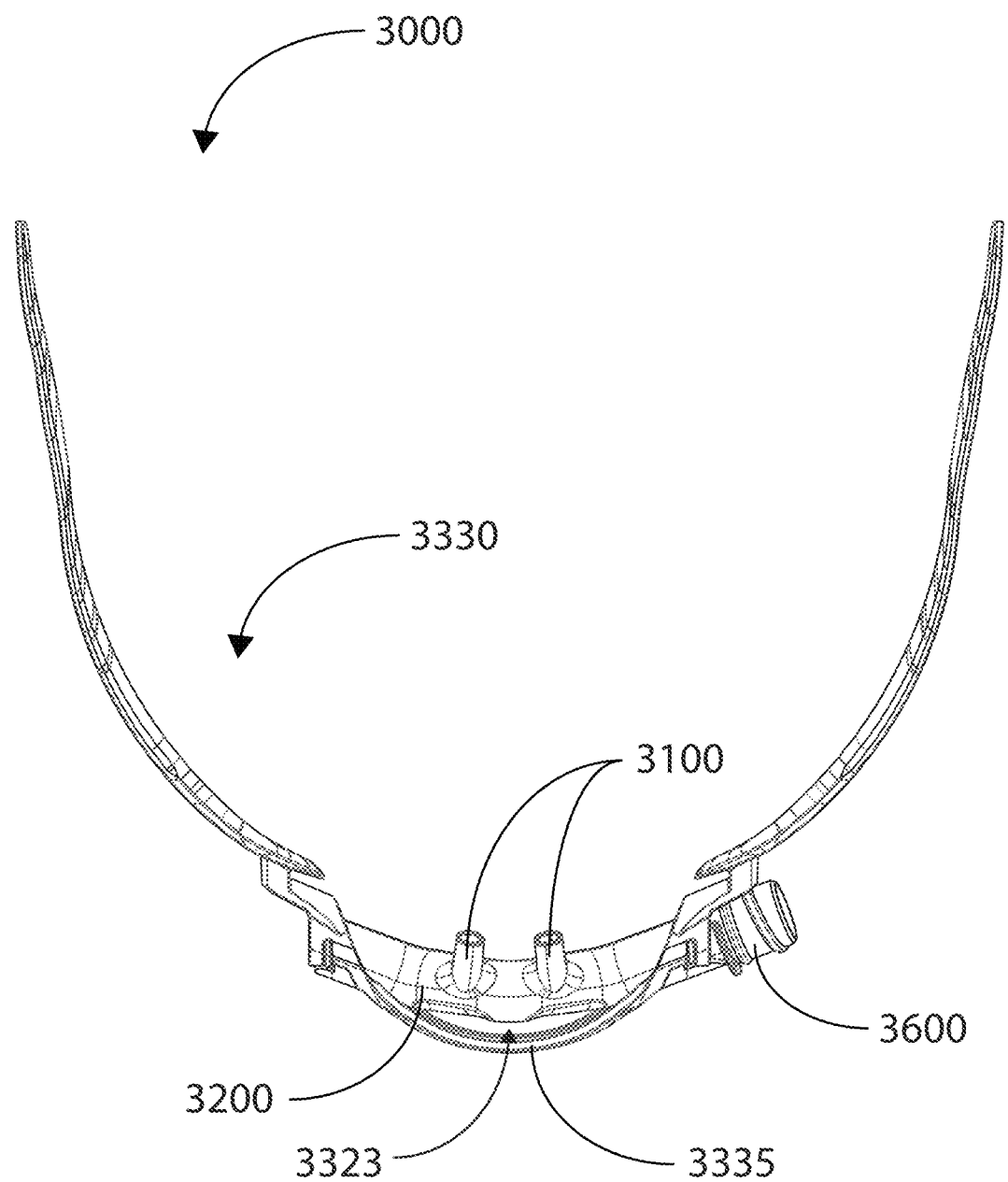

FIG. 4J shows a top (plan) view of a patient interface in the form of a nasal cannula in accordance with one form of the present technology.

Figure 4K:
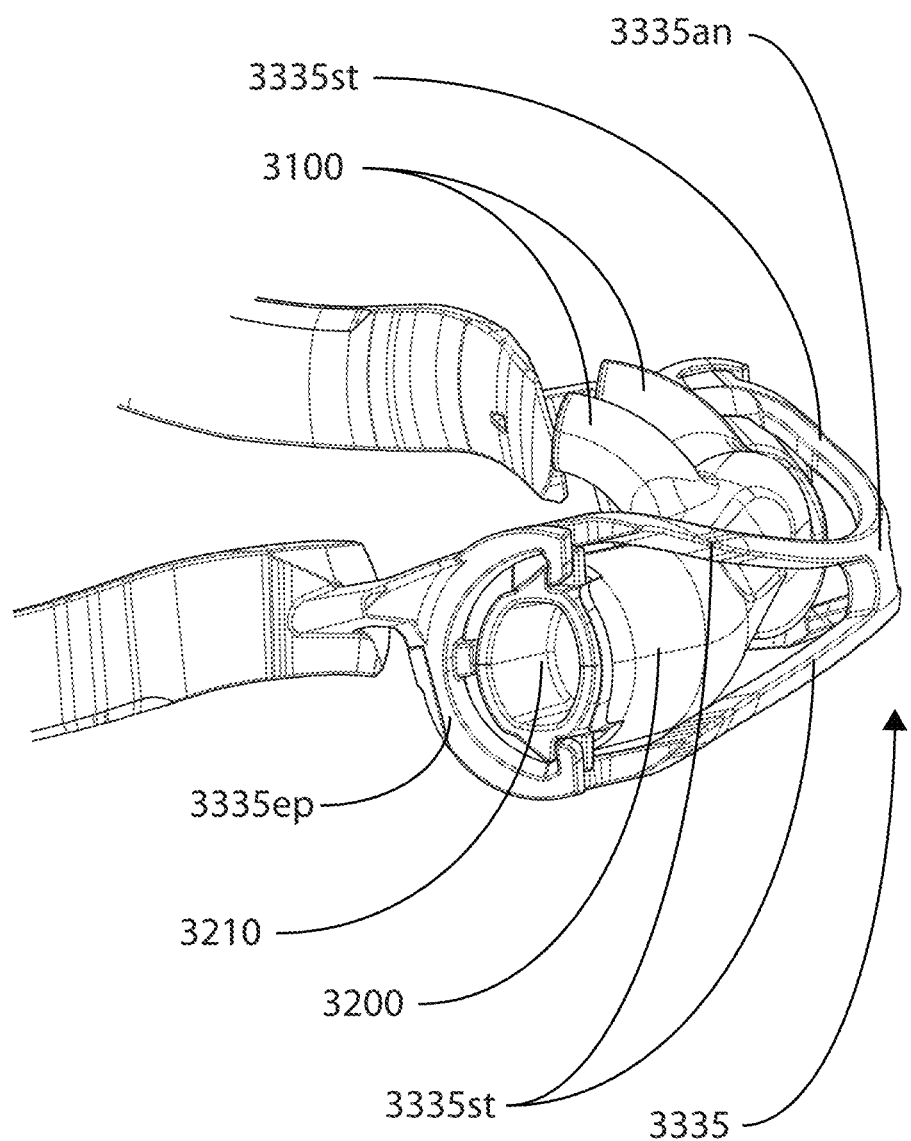

FIG. 4K shows a perspective view of a portion of a patient interface in the form of a nasal cannula in accordance with one form of the present technology.

Figure 4L:
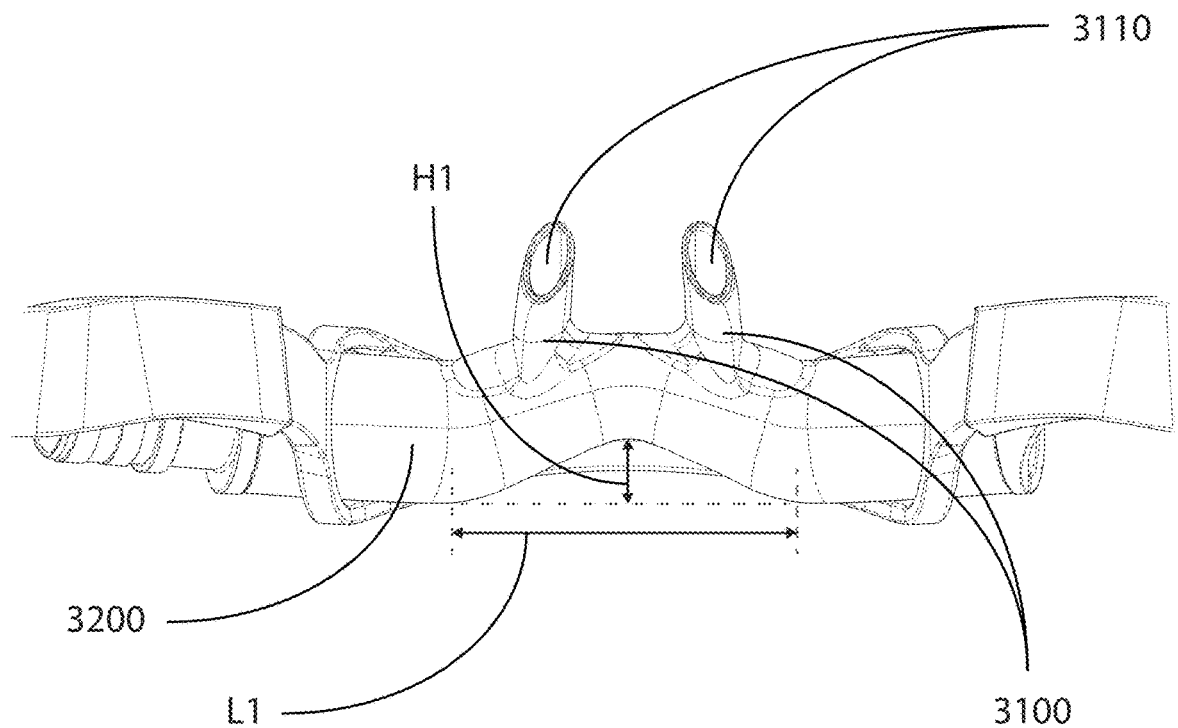

FIG. 4L shows a rear view of a portion of a patient interface in the form of a nasal cannula in accordance with one form of the present technology.

Figure 4M:
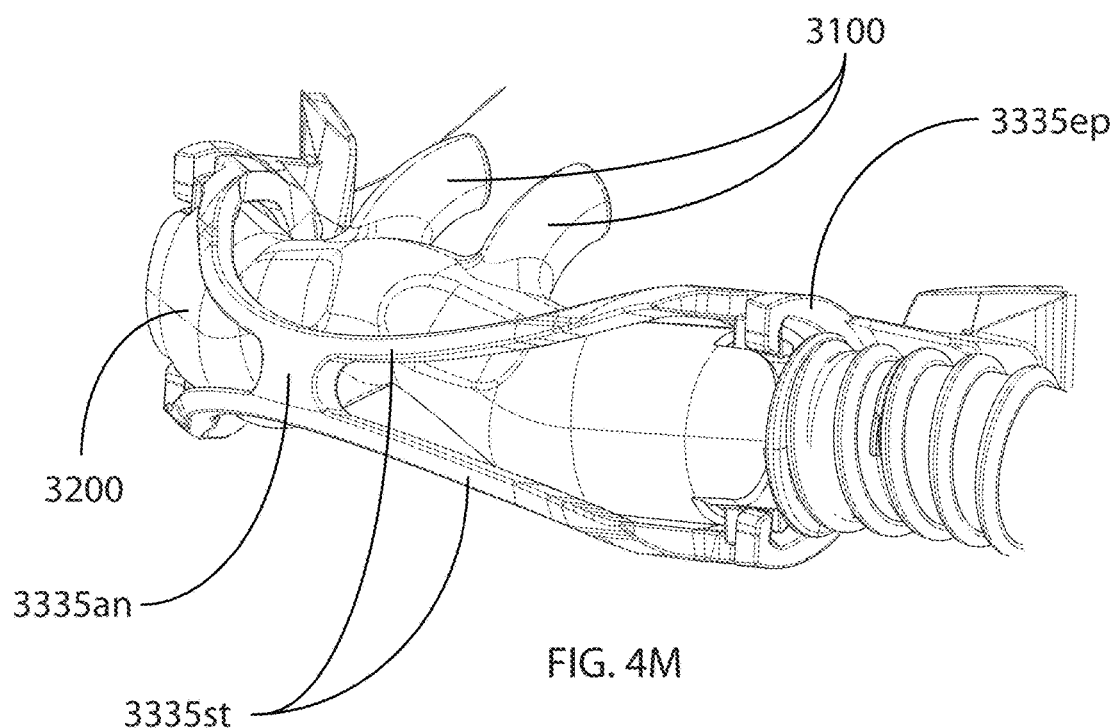

FIG. 4M shows a side perspective view of a portion of a patient interface in the form of a nasal cannula in accordance with one form of the present technology.

4.4 RPT Device

Figure 5A:
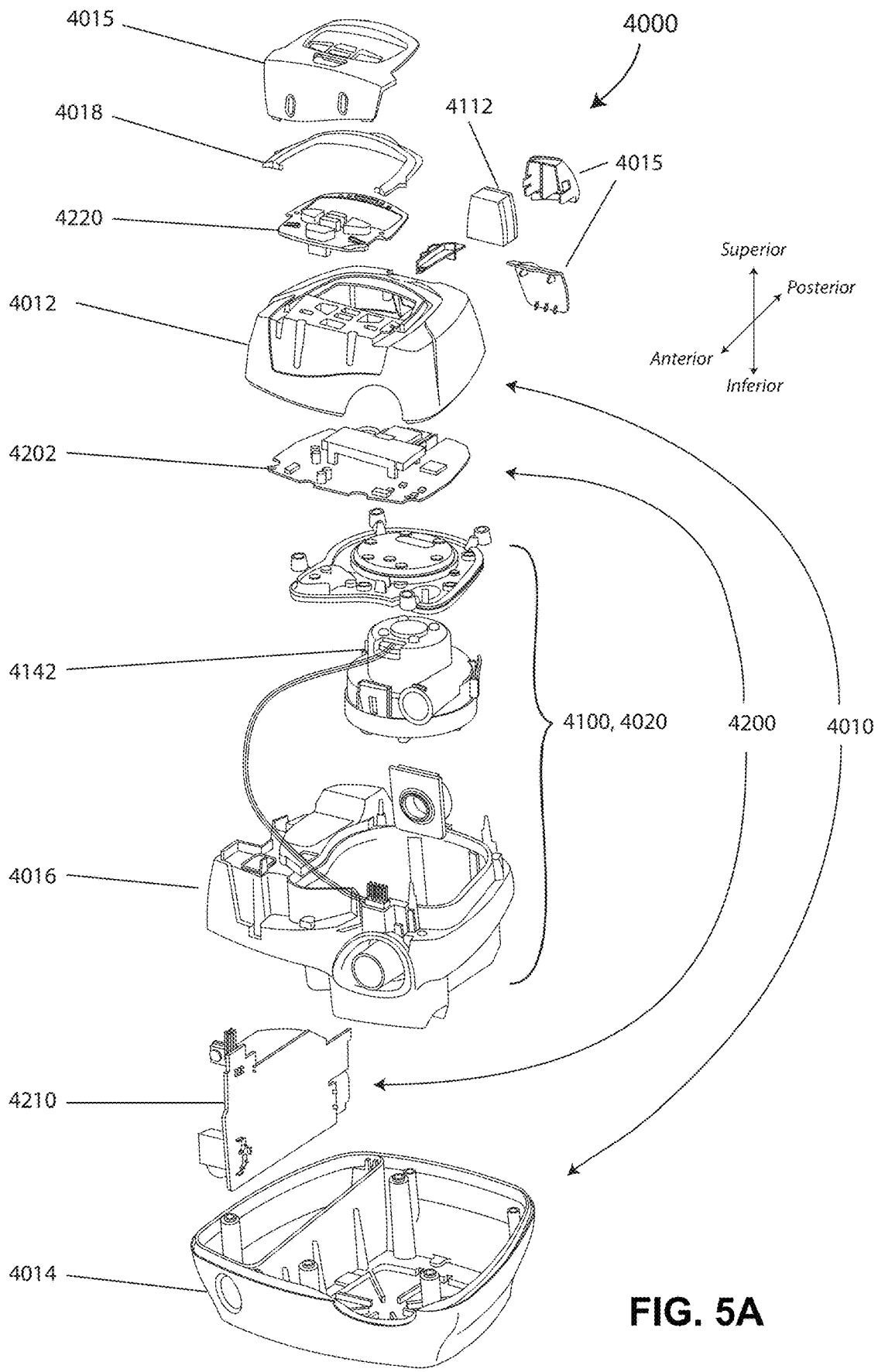

FIG. 5A shows an RPT device in accordance with one form of the present technology.

4.5 Humidifier

Figure 6A:
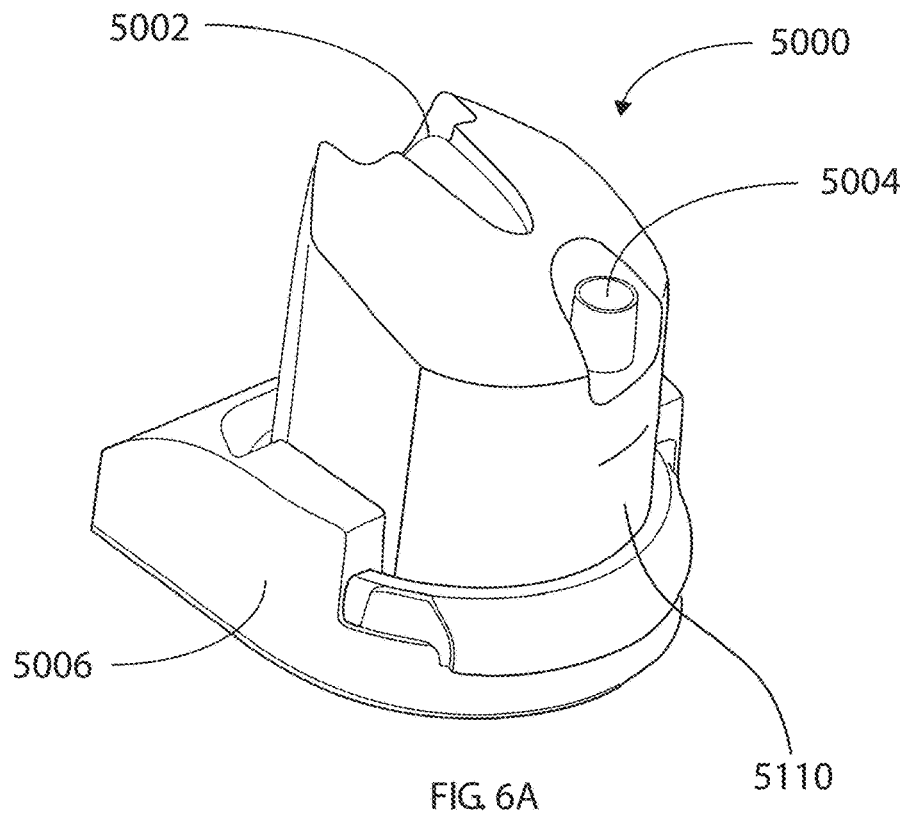

FIG. 6A shows an isometric view of a humidifier in accordance with one aspect of the present technology.

Figure 6B:
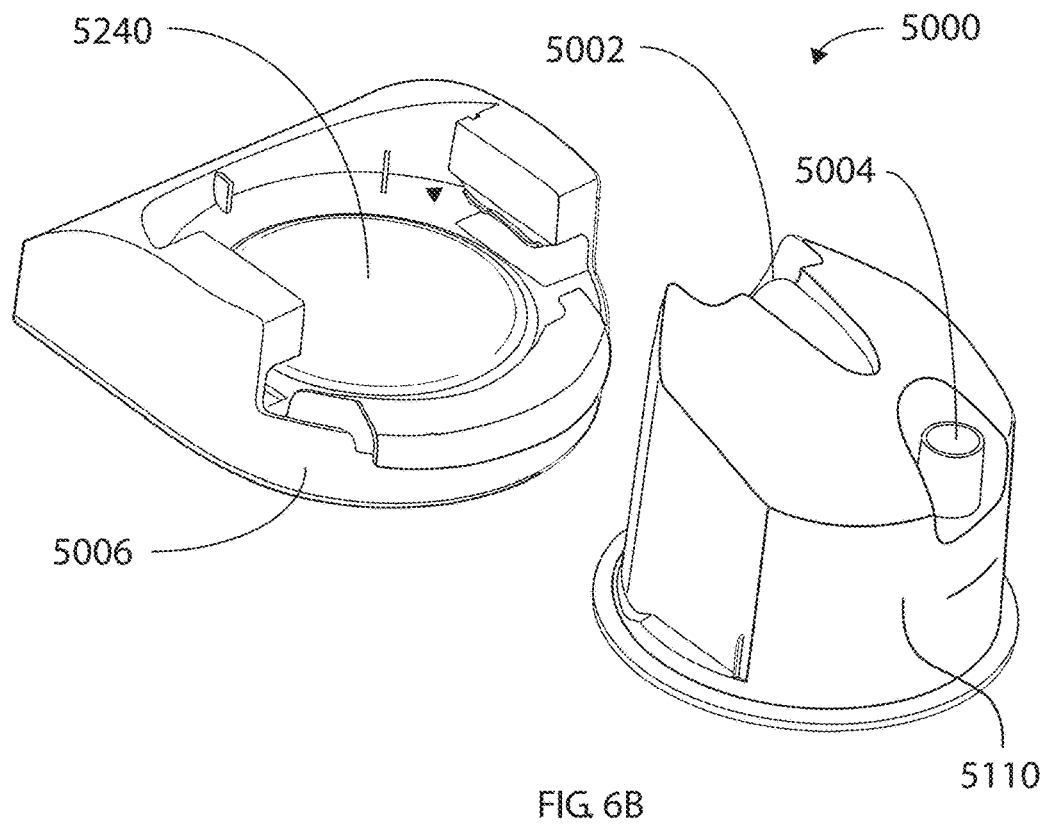

FIG. 6B shows an isometric view of a humidifier in accordance with one aspect of the present technology, showing a humidifier reservoir 5110 removed from the humidifier reservoir dock 5130.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

5.1 Therapy

In one form, the present technology comprises a method for treating a respiratory disorder comprising the step of applying positive pressure to the entrance of the airways of a patient 1000.

In certain embodiments of the present technology, a supply of air at positive pressure is provided to the nasal passages of the patient via one or both nares.

In certain embodiments of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised respiratory gas, such as air, to the patient 1000 via an air circuit 4170 to a patient interface 3000.

5.3 Patient Interface 3000

A non-invasive patient interface 3000 in accordance with one aspect of the present technology comprises the following functional aspects: an air directing structure, a positioning and stabilising structure 3300 and a connection port 3600 for connection to air circuit 4170. In some forms a functional aspect may be provided by one or more physical components. In some forms, one physical component may provide one or more functional aspects.

5.3.1 Air Directing Structure

An air directing structure may direct a flow of air received by the patient interface 3000 to the patient's airways such as via at least one of the nose or the mouth.

Figure 1A:
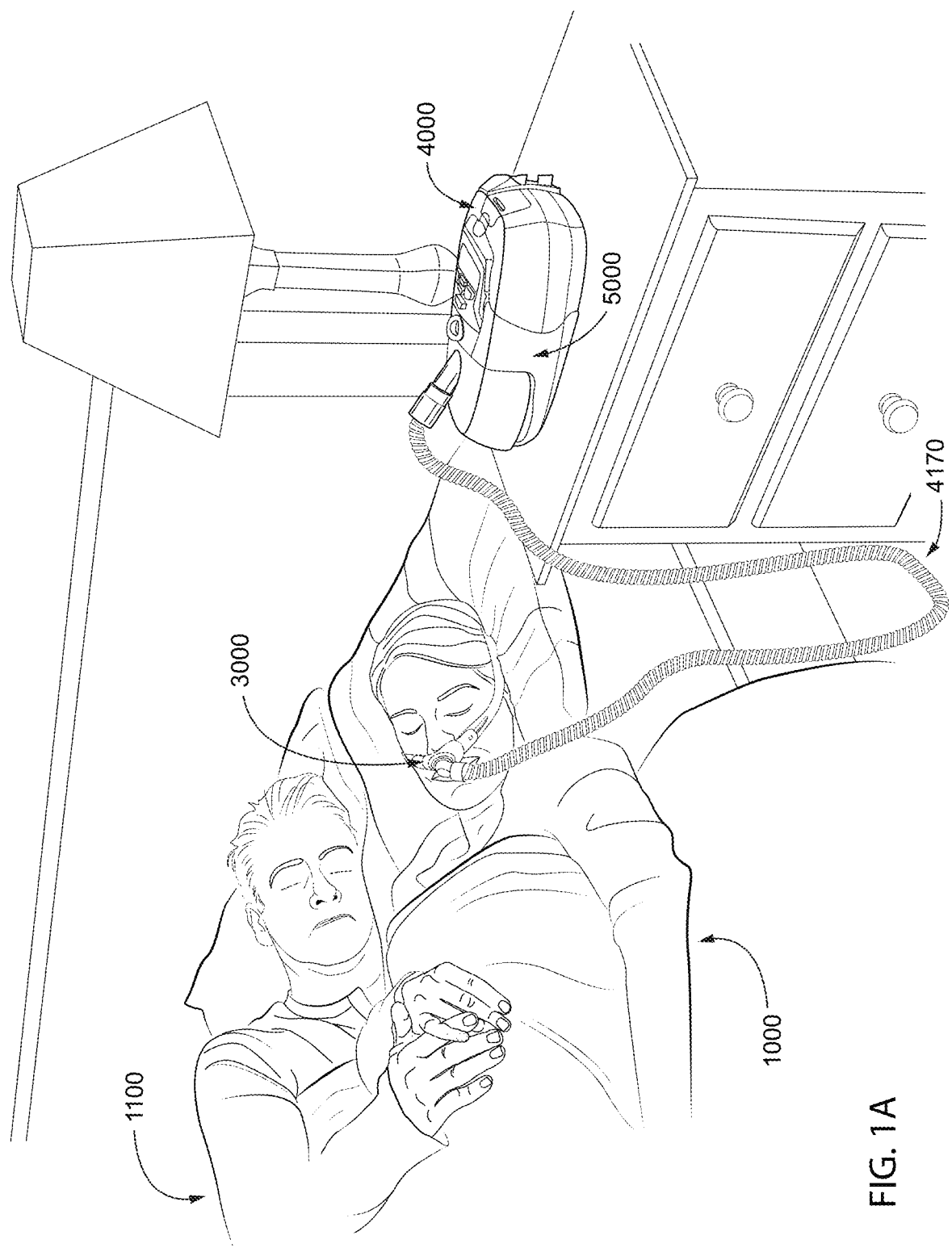
FIG. 1B shows a system including a patient 1000 wearing a patient interface 3000, in the form of a nasal mask, receives a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receives a supply of air at positive pressure from an RPT device 4000. Air from the RPT device is humidified in a humidifier 5000, and passes along an air circuit 4170 to the patient 1000.
Figure 1B:
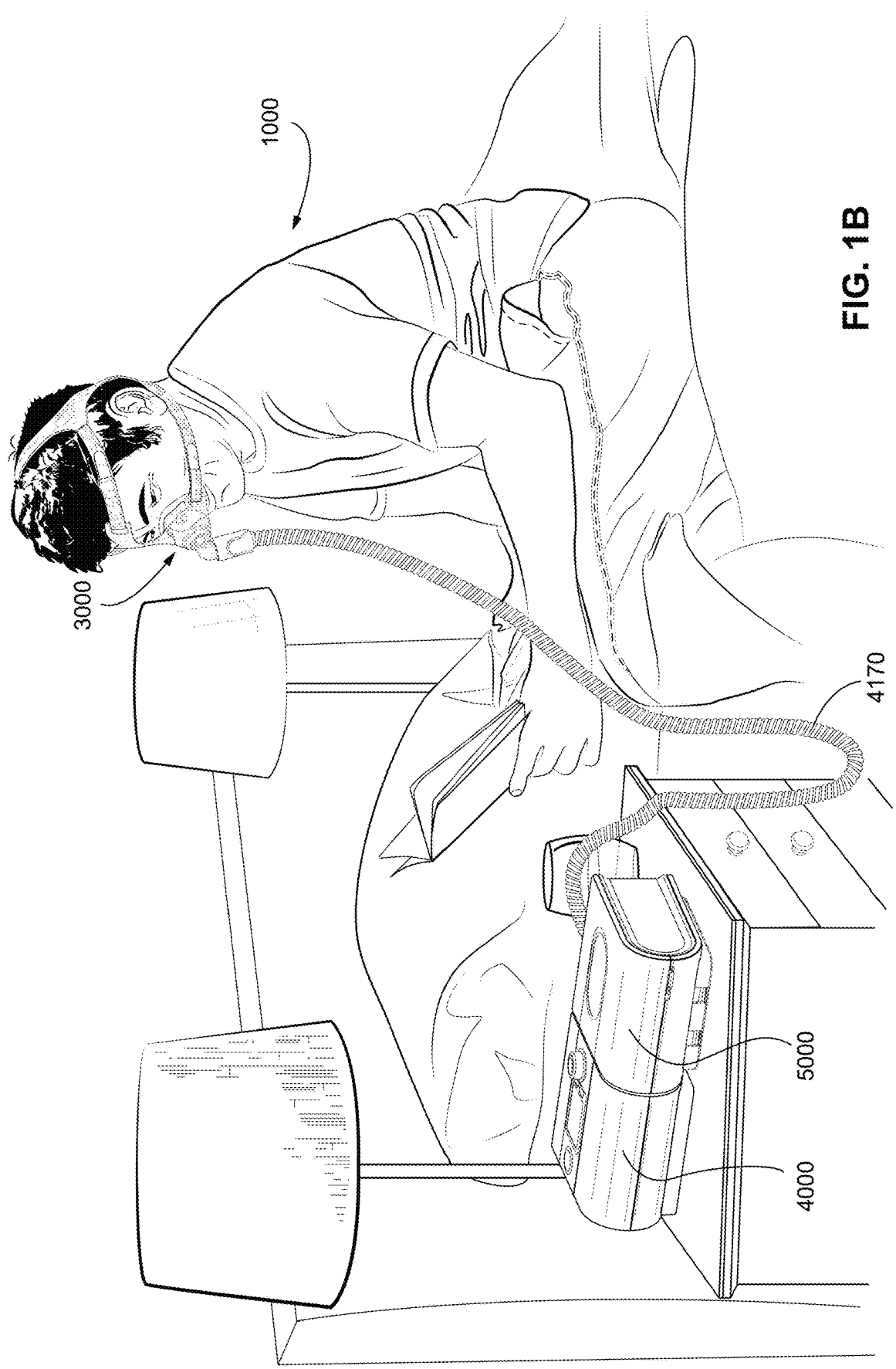
Figure 1C:

In some forms, an air directing structure may comprise one or more walls configured to form a sealed conduit to the patient's airways (e.g. a nasal pillows, a nasal mask or a full face mask as shown in FIGS. 1A-1C), thereby directing a flow of air to the patient's airways such as a mouth or the nares.

In other forms, an air directing structure may direct air into the one or more nares of the patient 1000 without forming a sealed conduit. For example, a nasal cannula may deliver a flow of air to the patient 1000, wherein the prongs of the nasal cannula are placed near or in the nares of the patient without forming a seal thereto.

According to one aspect of the present technology, the air directing structure may comprise one or more nasal prongs 3100 as shown in FIG. 3A configured to direct a flow of air into one or more nares of the patient 1000.

In one form, the nasal prongs 3100 may be configured to be inserted into nasal cavity of the patient 1000. In an example shown in FIG. 4I, a portion of the nasal prongs 3100 is shown in broken lines to indicate that it is inserted into a nasal cavity of the patient 1000. In other forms, the nasal prongs 3100 may be located outside of the nasal cavity of the patient 1000 and direct air into the one or more nares of the patient 1000.

A nasal prong 3100 according to one form of the present technology may be shaped to direct the flow of air into the patient's nares, and to minimise patient discomfort during use. As a nasal prong 3100 may be inserted into the patient's nasal cavity during use in some cases (see FIG. 4I, where a portion of the prong 3100 in the patient's nasal cavity is shown in broken lines), the nasal prong 3100 may be shaped to reduce a chance of the nasal prongs 3100 coming in contact with the patient, such as via the skin, or an interior of a nasal cavity. Preventing or reducing contact between a nasal prong 3100 and a patient may advantageously improve the patient's comfort in using the patient interface.

For example, the nasal prong 3100 may be configured to prevent contact with an interior surface(s) of the patient's nasal cavity or the lip superior (see FIG. 2C) during use. In one form, the nasal prong 3100 may be configured to approximate a curvature of the nasal cavity towards the nostril, thus extending in the superior and posterior direction towards the patient 1000. Examples of suitable shapes may include an arc as shown in FIG. 3H or FIG. 4C, however straight prongs or prongs comprising multiple sections (such as of varying curvature, shapes and/or directions) may be also suitable.

In one form, a nasal prong 3100 may be coupled to a plenum chamber (such as a manifold 3200) configured to receive a flow of air from one or more air circuits 4170. An example of a nasal prong 3100 coupled to a manifold 3200 is shown in FIG. 3A.

A manifold 3200 may include one or more openings to connect to one more air circuits. For example, the manifold 3200 may comprise an opening coupled to a connection port 3600 to connect to an air circuit. In some forms a manifold 3200 may be configured to connect to a plurality of air circuits, such as one or more air circuits for inspiratory flow and one or more air circuits for expiratory flow. The manifold 3200 may connect to an air circuit with a plurality of limbs, such as an inspiratory limb and an expiratory limb.

The prongs 3100 and the manifold 3200 may be constructed from an elastic, flexible and bio-compatible material such as silicone, although it will be understood that a number of other materials may be also suitable. In one form, the prongs 3100 and the manifold 3200 may be moulded, such as by injection moulding.

The prong 3100 and/or the manifold 3200 may be flexible, such as to reduce a discomfort of the patient when the prong and/or the manifold does come into contact with the patient, as will be described in further detail below.

The prongs 3100 and/or the manifold 3200 may comprise a relatively thin wall section. For example, the prongs 3100 and/or the manifold 3200 may be constructed from silicone by injection moulding, comprising a wall thickness of approximately 0.5 mm. Of course, it will be understood that other thicknesses may be also suitable, for example such as between approximately 0.2 mm and approximately 1 mm, between approximately 0.3 mm and 0.8 mm, or between approximately 0.4 mm and 0.6 mm. It will also be understood that a portion of the prongs 3100 and/or the manifold 3200 may comprise a different wall section thicknesses to another portion, such as according to structural requirements for the prongs 3100 and/or the manifold 3200.

In some forms, the manifold 3200 may be formed integrally with the nasal prongs 3100 as shown in exploded views of the patient interface 3000 in FIG. 3B or 4B. In other forms, the manifold 3200 may be formed separately to the nasal prongs 3100 and coupled thereto by at least one of any number of known means, such as by mechanical fasteners, adhesives or an interference fit.

Where the nasal prongs 3100 are coupled to the manifold 3200, the prongs 3100 may be movably coupled to the manifold 3200. That is, one or more prongs 3100 may be movable relative to the manifold 3200, for example in rotation about, or translation in, one or more axes. In one form, each prong 3100 may be independently movable relative to the manifold 3200 (and thus relative to the other prong(s) 3100), for example in rotation as shown in FIG. 3k.

Thus, a patient may move (e.g. rotate) one or more prongs 3100 relative to the manifold 3200 in order to orient the one or more prongs 3100 according to a preference of the patient, such as to suit the facial structure and/or nasal cavity of the patient. For example, the one or more prongs 3100 may be moved into a preferred operating orientation and/or location of the patient.

The patient interface 3000 may thereby be configured in an arrangement that may be comfortable for the patient, or that provides an improved delivery of the air flow to the patient's airways.

The manifold 3200 may provide structural support for the nasal prongs 3100. For example, the manifold 3200 may help to maintain the prongs 3100 in a position and/or orientation during use. The manifold 3200 may comprise a shape such as a cylinder to provide some structural support to the prongs 3100. The manifold 3200 may for example be configured as a straight cylinder.

The position and/or orientation of the prongs 3100 during use may include in or near the nares of the patient 1000, such as directed towards the one or more nares of the patient 1000.

In use, the manifold 3200 may be located close to, or on the patient 1000 in order to effectively maintain the prongs 3100 in a preferred operating position and/or orientation, such as with respect to the nares of the patient. For example, the manifold 3200 may be located close to the lip superior of the patient 1000, in an orientation such that the prongs 3100 may be directed towards the nares of the patient and/or the nasal cavity of the patient.

An arrangement of a patient interface 3000 wherein the manifold 3200 is in proximity to the patient's lip superior (and thus to the nares) allows an effective delivery of the flow of air to the patient's airways with the prongs 3100 of a relatively short length such as a length between the nares and the manifold. In turn, the short length may advantageously increase a rigidity of the prongs 3100, thereby assisting the prongs 3100 to remain in a predetermined configuration in relation to the manifold 3200.

In some cases, as a result of the close location of the manifold 3200 to the patient's lip superior, the manifold 3200 may apply a pressure (or force) on the patient 1000 during use of the patient interface 3000. Such a pressure (or force) may cause at least some discomfort to the patient 1000 during use of the patient interface 3000 due to the tactile sensation of the pressure. Furthermore, while the lip superior region provides a proximate wall to locate the prongs 3100 with respect to the patient's nares, it is also typically a sensitive region of the face for many patients.

Thus, a patient interface 3000 according to the present technology may be configured to be located close to, or on the patient 1000 to provide a flow of breathable gas to the patient 1000. Further advantageously, the patient interface 3000 may also minimise pressure (or force) applied to sensitive region(s) of the patient 1000, such as the lip superior and/or the subnasale.

In one example, a patient interface 3000 may be arranged so that the manifold 3200 is compliant in a direction of engagement to the patient's face (e.g. anterior direction), for example by inclusion of predetermined flexing joints or low-stiffness regions in the manifold 3200. Stiffness may be expressed in some cases as a spring rate, thus such a manifold 3200 could be said to have a reduced spring rate.

In another example, the manifold 3200 may be flexibly coupled (e.g. in at least the anterior direction) to a frame of the patient interface 3000. A manifold 3200 in such arrangements may thus reduce a pressure (or force) applied to an area of the patient's face in contact with the manifold 3200.

A pressure (or force) generated by a deformation of an object may be a function of a stiffness of an object that is deflected. Thus, a manifold 3200 configured to be compliant in at least an anterior direction may be advantageous in that when the manifold 3200 comes in contact with the patient 1000, such as when deformed or displaced in the anterior direction, a resulting pressure (or force) applied to the patient at a region of contact may be reduced.

For example, when a manifold 3200 comes in contact with the face of the patient 1000 (e.g. at or near the lip superior or the subnasale), a displacement or deformation of the manifold 3200 may occur. The displacement or deformation of the manifold 3200, from its resting condition, may occur as the patient interface 3000 is placed on the patient in its operating configuration. The displacement or deflection may be in an anterior direction, in which case the resulting pressure (or force) on the patient 1000 may be a function of a stiffness of the manifold 3200 in the anterior direction. Thus, by reducing the stiffness of the manifold 3200 in the anterior direction, a pressure (or force) on the lip superior or the subnasale of the patient 1000 may be reduced to improve patient comfort. Similarly, the manifold may be configured to readily displace or deflect in one or more other directions (e.g. by comprising a reduced stiffness), patient comfort may be improved.

Thus, one aspect of the present technology relates to a patient interface 3000 comprising a low-stiffness portion. Some examples of the present technology may comprise a manifold 3200 comprising a central portion with a reduced stiffness in comparison to one or more other portion of the manifold 3200, such as adjacent portions, or the entirety of the manifold 3200. The low-stiffness portion may comprise a reduced stiffness in at least the anterior direction.

The low-stiffness portion may comprise a reduced stiffness in comparison to another portion of the manifold 3200 by one or more of a plurality of mechanisms, such as by geometric or material means. For example, the low-stiffness portion may comprise a reduced wall thickness, comprise a material with a lower elastic modulus and/or comprise a shape with a lower stiffness (e.g. in bending) relative to another portion of the manifold 3200.

In some forms, the low-stiffness portion may comprise a connection portion between adjacent portions. For instance, a first portion of a manifold 3200 may be coupled to an adjacent portion of the manifold 3200 by a low-stiffness portion, such as portion of reduced wall thickness, material stiffness or low-stiffness geometry such as a hinge portion.

The manifold 3200 may comprise a cylindrically shaped body, for example as shown in FIG. 3A. Alternatively, the manifold 3200 may comprise a curved body as shown in FIGS. 4B and 4D, wherein the body is curved to approximate a curvature of a patient's face.

In one form, as shown in FIGS. 4B-4D, the manifold 3200 comprises one or more 'grooves', such as a front indent 3200*fi* and a rear indent 3200*ri*. The one or more grooves may be configured to comprise a reduced stiffness as described previously. One or more of the indents 3200*fi* and 3200*ri* may (e.g. as shown in FIG. 4D) extend substantially along a sagittal plane, thus perpendicularly to the anterior direction. The groove(s) may thereby reduce a stiffness of the manifold 3200 in the anterior direction. The indents 3200*fi* and 3200*ri* may thus provide additional compliance to the manifold 3200 when the manifold 3200 is displaced or deformed in the anterior (or posterior) direction, such as due to a movement of the patient's upper lip, or due to fitment of the patient interface 3000 onto the patient's face. The indents 3200fi and 3200ri may additionally or alternatively comprise a reduced wall thickness in comparison to the adjacent portions of the patient interface 3000, such as the rest of the manifold 3200.

For example, the grooves may assist in preventing the manifold 3200 from becoming taut. If the manifold 3200 was to become taut, it may lead to reduced resistance (effective spring rate) on the manifold 3200 and exhibit greater reaction forces on the face of the patient, for example when displaced or deformed further.

At a reduced stiffness portion of the manifold, such as that comprising the indents 3200fi and 3200ri, the cross-section width (viewed from the anterior direction) may be for example approximately 50% of a typical width in the adjacent portion (see FIG. 4D). In other forms, the cross-section width may be approximately 40-60%, or 25-75% of a typical width. It will be understood that other aspects of the material or geometry may be varied to achieve an appropriate reduction in stiffness as described elsewhere.

According to one aspect, a base of the manifold 3200 may comprise a raised central portion as shown in FIG. 4L. The raised central portion may comprise an indent at the base of the manifold 3200, for example with a length of L1 and a height of H1 as shown in FIG. 4L. The raised central portion may improve a patient's comfort by reducing interference between the face of the patient (e.g. the upper lip) and the manifold 3200.

In one example, the raised central portion may approximately span 30 mm, and raised by approximately 6 mm as shown in FIG. 4L. In other forms, the raised central portion may approximately span between 25 mm and 35 mm, or further alternatively may approximately span between 15 mm and 45 mm Additionally, or alternatively, the raised central portion may be raised by approximately between 5 mm and 7 mm, or between 4 mm and 8 mm, or between 3 mm and 9 mm It will be understood by those skilled in the art that any number of other methods and/or mechanisms may be employed while achieving a goal of reducing a pressure and/or force on the sensitive region of the face, such as the lip superior or the subnasale region. For example, an effective spring rate of the manifold 3200 in the direction of engagement with the face may be reduced, using one or more a reduced local wall thickness, a concertina section, use of a different (e.g. softer) material, a flexible joint or a curved geometry.

The patient interface 3000 may comprise one or more manifold caps 3210 configured to couple to an end of a manifold 3200. A manifold cap 3210 may be closed, to couple to an end of a manifold 3200 and form a wall. In some forms, a manifold cap 3210 may comprise a connection port 3600 to allow therethrough, to connect the manifold 3200 to an air circuit 4170 to receive or deliver a flow of air. A manifold cap 3210 may be inserted into the manifold 3200 for a secure fitment, however many other forms of connections may be also suitable.

In a form as shown in FIG. 4B, the manifold 3200 may be connected to a first manifold cap 3210 configured to close a first end of the manifold 3200, and a second manifold cap 3210 comprising a connection port 3600 for connecting to an air circuit 4170.

A manifold cap 3210 may further comprise a connecting means to locate and/or secure the manifold 3200 to the positioning and stabilising structure 3300. The connecting means may be a latch such as shown in FIG. 4B or FIG. 4K. The manifold cap 3210 may be configured to engage a positioning and stabilising structure 3300, as shown in FIG. 4B and FIG. 4K for example, such as via an end portion 3335ep.

The end portion 3335ep may comprise a receiver portion of the latch as shown in FIG. 4K, although any number of other arrangements may be also suitable. The latch may comprise a lead-in to allow ready assembly while discouraging disassembly of the manifold cap 3210.

According to another aspect, a nasal prong 3100 may be configured to be able to move relative to the positioning and stabilising structure 3300 of the patient interface 3000. In one form, the manifold 3200 may be coupled to a rotating barrel 3150 as shown in FIGS. 3A-3B, where the barrel 3150 may be rotatably engaged with a positioning and stabilising structure 3300 or a part thereof, such as the front brace 3320 as shown in FIGS. 3H-3I.

The barrel 3150 and the front brace 3320 may be rotatably engaged so that an adjustment of relative rotation may be discretely variable (e.g. by notches 3152 and protrusion 3322 as shown in FIG. 3H and FIG. 3I), or continuously variable, for example by a sliding friction fit (not shown).

The barrel 3150 in one form may include a grip 3150gr to allow easy rotation of the barrel 3150 with one hand. The grip 3150gr may comprise one or more recesses configured to receive fingers of the patient 1000 (or another user), or a high-friction surface to improve engagement of the fingers with the grip 3150gr.

The barrel 3150 may comprise one or more ends, each end for example configured to close an end of the manifold 3200 or provide a connection port 3600. For example, the exemplary barrel 3150 shown in FIG. 3B comprises a first, closed end configured to form a wall at a first end of the manifold 3200, and a second, open end configured to connect to a connection port 3600. The first end of the barrel 3150 shown in FIG. 3B comprises a grip 3150gr, although the grip 3150gr may be placed on the second end in some forms.

Each nasal prong 3100 may comprise one or more openings 3110 for delivering the flow or air to the patient's airways. In one form, the openings 3110 may be configured in an elliptical shape as shown in FIG. 3C, although it would be understood by those skilled in the art that other shapes or configurations may be also suitable.

5.3.2 Positioning and Stabilising Structure 3300

The air directing structure of the patient interface 3000 of the present technology may be held in an operating position by the positioning and stabilising structure 3300. In one form, the positioning and stabilising structure 3300 may comprise a frame (e.g. two side braces 3310 and a front brace 3320) and a headgear (e.g. a rear strap 3350 and a top strap 3340) as shown in FIG. 3A. The positioning and stabilising structure may be configured to hold the air directing structure in its operating position and/or orientation in use, while minimising any potential disturbances to the patient. In one form, the positioning and stabilising structure 3300 may be configured to apply minimal pressures on the upper lip (lip superior) or the subnasale region of the patient 1000 as will be described in further detail below.

5.3.2.1 Frame

The patient interface 3000 may comprise a frame rigidly configured to act as a skeleton to the patient interface 3000, such as by maintaining a shape and/or configuration of the patient interface 3000 in one or more directions or aspects. The frame may be configured to engage the face of the patient 1000 in use, such as the left and right cheeks of the patient 1000. In some forms, a frame may be constructed from polypropylene or polycarbonate, such as by moulding.

The positioning and stabilising structure 3300 in some configurations may thus comprise a frame configured to engage at least a patient's cheeks when the patient interface 3000 is in an operating position and/or orientation, such as when the patient interface 3000 is in use.

The frame may be configured further such that a stiffness of the frame in a direction (e.g. anterior direction) is higher than a stiffness of another portion of the patient interface 3000. For example, the stiffness of the frame at the location of engagement with the patient's cheek(s) may be higher than a stiffness of the patient interface (e.g. manifold 3200) for engagement with the lip superior.

In an exemplary configuration, forces applied by the positioning and stabilising structure 3300 to locate and support the patient interface (in particular, the nasal prongs 3100) on the patient 1000 (supporting load) may advantageously be reacted primarily on the cheeks, where the patient 1000 may be generally be less sensitive to pressure than for example the patient's lip superior.

The patient interface 3000 at the cheek-engaging region may be thus stiffer in comparison to the lip superior-engaging region by one of a number of possible ratios in at least one direction (e.g. in the anterior direction). For example, the cheek-engaging region may be stiffer by an approximate factor of two, five, ten, or twenty. It will also be understood that this ratio may be varied according to the particular arrangement of the patient interface. Some exemplary aspects that may affect the ratio may include such as a size of a contact area of the cheek-engaging region and/or the lip superior-engaging region or whether the lip superior-engaging region is in constant engagement with the lip superior while the patient interface 3000 is in use, as the lip superior-engaging region (e.g. the manifold) may not always be engaged with the lip superior.

In one form, as shown in FIG. 3E, each side brace 3310 may comprise a curved cheek-engaging region 3310ch. The side brace 3310 may be rigidly configured so that the supporting load may be transferred to (and reacted by) the cheek of the patient where the side brace 3310 engages with the cheek. For example, the side brace 3310 may be rigidly configured relative to a manifold 3200 and/or the prongs 3100 which may be constructed from a softer material such as silicone.

The side brace 3310 may be relatively thin in a direction extending along the surface of the face in order to allow the side brace 3310 to bend and follow the contour of the face, while in other directions (e.g. in the vertical direction) the side brace may be thicker to resist deformation. Such an arrangement may allow one shape of the side brace 3310 to be suitable for a plurality of face shapes of a patient. In some forms, the frame (including, for example the side brace 3310) may be pre-formed with curves (e.g. as shown in FIGS. 3D-3E) to follow typical curvatures of the face, while allowing for sufficient flexibility for adjustability where variability in shape may be required.

According to another aspect, the patient interface 3000 may further comprise a rigid front portion, such as the front brace 3320 as shown in FIGS. 3A-3B, which connects the two side braces 3310. The front portion may be present in addition to the manifold 3200 which may also be present between the two side braces 3310. The manifold 3200, however, may be flexibly configured to structurally be de-coupled from the frame, such as the front brace 3320 and/or the side braces 3310.

Thus, in some forms, a patient interface 3000 may comprise a rigid front portion (e.g. front brace 3320) and a manifold 3200, both of which may extend across the face (perpendicularly to the sagittal plane). The manifold 3200 may be closely located to the patient's face for effective delivery of the breathable gas, while the front portion may be configured to connect the left and right sides of the patient interface.

In some forms, the front portion may be recessed from the patient 1000, in a direction away from face of the patient 1000 (for example in relation to the lip superior). Thus the front brace 3320 may be recessed as shown in FIG. 3E in the anterior direction (see FIG. 2D. for directional reference) from the patient 1000.

In one form, the front brace 3320 may comprise a central portion 3325 and one or more side portions 3327. The central portion 3325 may extend across the patient's face while recessed from the manifold 3200. The one or more side portions 3327 (e.g. a left side portion and a right side portion) may be configured to engage and/or attach with the side brace(s) 3310.

The front portion may be either or both rigidly configured and rigidly coupled to the cheek-engaging portion(s) of the frame (e.g. side brace 3310) to help maintain the cheek-engaging portion(s) in their preferred operating position and/or orientation inuse.

In the example shown (see FIG. 3E), the front brace 3320 engages the side braces 3310 such that the frame as a whole is rigidly constrained in the lateral direction (i.e. across the sagittal plane).

The front portion of the frame may be configured to reduce discomfort which may be caused by the nasal prongs 3100 and the manifold 3200 on the patient 1000.

The front brace 3320 may comprise a recess with respect to the manifold 3200 in one or more directions (e.g. in the anterior direction). In such a configuration, any interference of the manifold 3200 with the patient's face (e.g. on the lip superior) may cause the manifold 3200 to be deformed or displaced in the anterior direction as described above.

In examples shown in FIG. 3E and FIG. 3F, the front brace 3320 is shown to comprise a recess 3323 between the manifold 3200 and the front brace 3320 (e.g. to a centre of the central portion 3325) the in the anterior direction. The recess 3323 may thus provide space for the manifold 3200 to move into, when deformed or displaced in the anterior direction, such as may be caused by contact with the lip superior of the patient 1000.

Advantageously, the deformed or displaced manifold 3200 may not come into contact with the front brace 3320 as the deformation and/or displacement may occur into the recess. Accordingly, the resisting force on the patient's face in this configuration may be reduced in comparison to a configuration where the manifold 3200 may be pushed against a rigid boundary such as the front brace 3320.

Yet further, provision of such a recess between the manifold 3200 and the front brace 3320 allows the manifold 3200 to be displaced in the anterior direction without collapsing (e.g. undergoing a significant reduction in cross-section area), so that potential occlusion of the air flow path may be prevented. This may be further advantageous by reducing any potential for changes to delivery of the flow of air to the patient 1000.

Provision of one or more recesses as described above may be further advantageous in fitment of the patient interface 3000 to the patient 1000. It is well known that a shape of the patient's head and face will vary according to the individual patient, creating a range thereof that a patient interface 3000 need to accommodate. A patient interface 3000 comprising one or more recesses as described above may help to accommodate variations in shapes of the head and face patient 1000.

For example, the one or more recess may allow the manifold 3200 and the nasal prongs 3100 to move relative to the face of the patient 1000 while maintaining a relatively constant pressure on sensitive areas of the face, thus reducing the sensitivity of degree of discomfort to facial variations.

A recess between the manifold 3200 and the front brace 3320 may be for example approximately between 1-4 mm, such as 2-3 mm, such as 2.5 mm. In some forms, the recess may be larger or smaller, and it will be understood that the size of the recess may be varied from the examples discussed herein, for example according to a particular arrangement and/or configuration of the patient interface 3000.

In one form of the present technology, a positioning and stabilising structure 3300 may comprise a brace 3330 as shown in FIG. 4B. The brace 3330 may comprise a central portion 3335 as will be described in further detail herewithin.

The central portion 3335 may comprise one or more strut members 3335st such as shown in FIG. 4G. A strut member 3335st of the central portion 3335 may be configured to surround the manifold 3200 as shown in FIG. 4H. As shown in the examples of FIGS. 4B and 4G, the central portion 3335 may at least partially surround the air directing structure such as the manifold 3200.

In one form, one or more strut members may join to form a triangulated portion. In some examples, one or more sides of the triangulated structure may be curved, such as to result in a substantially teardrop-shaped cavity. A structure may be substantially non-planar while still being considered 'triangulated'.

An example of the central portion 3335 shown in FIG. 4G may thus be said to comprise two out-of-plane, teardrop-shaped structures, which would nonetheless be considered to be triangulated.

As shown in FIG. 4G and FIG. 4H, the central portion 3335 may comprise two triangulated structures extending across the manifold in the anterior and posterior direction. The triangulated structures may be joined at or near the sagittal plane, such as by strut members 3335st converging towards a common anchor portion 3335an as shown in FIG. 4G and FIG. 4H.

A plurality of strut members 3335st may thus extend from a width of at least a height of the manifold 3200, to an anchor portion 3335an. In some forms, there four strut members 3335st may converge at a single, central anchor portion 3335 as shown in FIG. 4G and FIG. 4H, creating a triangulated structure that is rigid in the superior and inferior directions while remaining lightweight.

Each set of strut members may be joined at distal ends to the anchor portion 3335an by an end portion 3335ep to form a triangulated, looped structure. The end portion 3335ep may comprise a curved portion that is complementarily formed to the manifold 3200 to surround the manifold 3200. Thus, the example shown in FIG. 4H shows the manifold 3200 to traverse through a triangulated structure of the central portion 3335.

Although the central portion 3335 is shown in FIGS. 4G and 4H to comprise two triangulated portions, it should be noted that other forms may also be possible. It is noted that although in the shown examples, the anchor portion 3335an, the strut members 3335st and/or the end portion 3335ep are integrally formed with each other, other arrangements may be possible.

Additionally, or alternatively, the central portion 3335 may comprise a curve. The central portion 3335 may be curved in one or more planes, such as when viewed from a plane normal to the superior direction (e.g. from above the head when worn by a patient, such as in an orientation shown in FIG. 4J). As shown in FIG. 4D, the central portion 3335 may comprise a curve with a radius of approximately 30 mm It will of course be understood that other radii may be also suitable, such as ranges of approximately between 20-50 mm, 25-40 mm, 30-35 mm or other radii. The suitable radius may be chosen according to a number of other parameters of the patient interface 3000, such as the intended patient demographic, rigidity of the other portions of the patient interface 3000, size of the manifold 3200 or the type of patient interface 3000.

The central portion 3335 may be configured to be more rigid in one direction than in another. In one form, the central portion 3335 may comprise a higher bending stiffness in one direction than in a second, orthogonal direction.

For example, the central portion 3335 may be significantly stiffer in reaction to a bending moment caused by a force in a superior direction than to a bending moment caused by a force in an anterior direction. Such a configuration may advantageously allow the patient interface 3000 to conform to a face of the patient 1000 without imposing a significant force and/or pressure (and thus discomfort) to the patient.

In one form, the said disparities in stiffness may be achieved at least in part by configuring the central portion to be triangulated in one direction (e.g. when viewed from the anterior direction), and not in a second, orthogonal direction (e.g. when viewed from the superior direction). An inspection of FIGS. 4E, 4G and 4J for example show that the patient interface 3000 is triangulated in one direction (e.g. as shown in FIG. 4E) and not in an orthogonal direction (e.g. as shown in FIG. 4J).

At least a portion of the central portion 3335 may extend past an exterior of the manifold 3200, such as can be seen in FIG. 4K and FIG. 4L. The central portion 3335 may extend past the exterior of the manifold in the anterior and posterior directions for example, as shown in FIG. 4J.

The central portion 3335 may be disengaged from the manifold 3200. The disengagement may allow the manifold 3200 to deform and/or a displace while maintaining a low stiffness to reduce a force and/or pressure on the patient as described in further detail elsewhere in the present document.

The central portion 3335 may extend across at least a part of the plenum chamber, such as across the manifold 3200 from left to right, for example spanning at least a part of the width of the manifold 3200. In some forms, the central portion 3335 may span across the entire (left-to-right) width of the plenum chamber while only engaging the plenum chamber at limited locations.

For example, the central portion 3335 may engage the plenum chamber at a left end and a right end of the plenum chamber as shown in FIGS. 4H, 4J and 4K, such as via the end portions 3335ep.

The central portion 3335 may in some forms overlap the manifold 3200 when viewed from above (e.g. as shown in FIG. 4J), while at least some of the overlapping portions of the central portion 3335 and the manifold 3200 may not engage each other.

The portion of the central portion 3335 that extends around and past the manifold 3200 may be curved as shown in FIG. 4D, although other forms and shapes may also be possible.

By extending around and/or past an exterior of the manifold 3200 without engagement, the central portion 3335 may provide a rigid structure for the patient interface 3000. At the same time, as the manifold 3200 may comprise a relatively low stiffness, thereby reducing discomfort of the patient 1000 during use.

In one example, the central portion 3335 and the manifold 3200 may be configured such that the rigidity of the patient interface 3000 may be negligibly affected by the presence of the manifold 3200. For example, the manifold 3200 may comprise a substantially cylindrical, thin silicone structure as described herein, whereas the central portion 3335 may comprise a plurality of triangulated struts.

Thus, only parts of the curved portion of the central portion 3335 may engage the manifold 3200, such as at the ends of the curved portion. It is noted that in some configurations of the technology, only a portion of the central portion 3335 may be curved.

Additionally, or alternatively, the patient interface 3000 may comprise a recess 3323 between the central portion 3335 and the manifold 3200 in the anterior direction (e.g. as shown in FIG. 4J). The central portion 3335 may be in some forms be configured such that a recess between the central portion 3335 and the manifold 3200 may vary in size across the sagittal plane. Accordingly, as the manifold 3200 deflects or deforms, the manifold 3200 may progressively come into contact with the central portion 3335, for example as a function of a deflection of the manifold 3200 in the anterior direction. This may have an effect of increasing a stiffness of the patient interface 3000 in the anterior direction in a progressive manner to provide a controlled increase in stiffness as well as feedback to the patient.

As described above (and shown in FIG. 3B), a frame may comprise a plurality of parts, such as a pair of side braces 3310 and a front brace 3320. However, it will be understood that a frame may comprise any number of parts such as one part, or a greater number of parts than the shown configurations. In some forms, the frame may also comprise a skeletal portion (3310*sk* in FIG. 3B or 3330*sk* in FIG. 4B) made of a rigid material and a cover portion made of a soft material (for example made of silicone or textiles) to improve the patient's comfort, particularly where the frame contacts the skin of the patient. The cover portion may be a silicone overmould (3310*om*) as shown in FIG. 3B or a textile cover (3330*tc*) as shown in FIG. 4B.

5.3.2.2 Headgear

Preferably, a headgear may be provided to engage the patient's head and assist to locate the nasal prongs 3100 with respect to the patient's nares. Various types and arrangements of headgear are known in the art, and it will be understood that there may be many suitable forms of headgear.

In one form as shown in FIGS. 3A-3J, the headgear may comprise a rear strap 3350 and a top strap 3340, which could be engaged to the frame using one of a number of known methods, such as adhesives, stitching, over-moulding and so on. In other forms, the headgear may be formed integrally with the frame.

Some forms of headgear (not shown) may engage the patient's ears for support, such as with one or more headgear portions, each of which loops or hooks around a base of the ear. Some forms of headgear (not shown) may include a single strap, such as to only include a rear strap. Yet other forms of headgear (not shown) may comprise one or more straps, each which may be for example bifurcated.

It will be understood that at least some forms of headgear that are previously known in the art may be combined with aspects of the present technology. For example, a bifurcated strap disclosed in PCT Patent Application Number WO/2014/015382 may be combined with a frame, manifold and prongs of the present technology.

5.3.3 Connection Port 3600

Connection port 3600 allows for connection to the air circuit 4170. In one form, the connection port 3600 may be located on the frame (e.g. see FIG. 3A or 4A), although a connection port 3600 may be located at the end of an air circuit 4170 as shown in FIG. 3B for connection to another air circuit 4170.

5.4 RPT Device 4000

A preferred RPT device 4000 in accordance with one aspect of the present technology comprises mechanical and pneumatic components 4100, electrical components 4200 and is programmed to execute one or more algorithms. The RPT device preferably has an external housing 4010, preferably formed in two parts, an upper portion 4012 and a lower portion 4014. Furthermore, the external housing 4010 may include one or more panel(s) 4015. Preferably the RPT device 4000 comprises a chassis 4016 that supports one or more internal components of the RPT device 4000. In one form a pneumatic block is supported by, or formed as part of the chassis 4016. The RPT device 4000 may include a handle 4018.

The pneumatic path of the RPT device 4000 preferably comprises an inlet air filter 4112, an inlet muffler, a pressure generator capable of supplying air at positive pressure (preferably a blower 4142), a pneumatic block and an outlet muffler. One or more transducers, such as pressure sensors and flow sensors may be included in the pneumatic path.

The preferred pneumatic block 4020 comprises a portion of the pneumatic path that is located within the external housing 4010 and may house the pressure generator 4140.

The RPT device 4000 preferably has an electrical power supply 4210, one or more input devices 4220, a central controller, a therapy device controller, a pressure generator, one or more protection circuits, memory, transducers, data communication interface and one or more output devices. Electrical components 4200 may be mounted on a single Printed Circuit Board Assembly (PCBA) 4202. In an alternative form, the RPT device 4000 may include more than one PCBA 4202.

Assembly (PCBA) 4202. In an alternative form, the RPT device 4000 may include more than one PCBA 4202.

5.5 Humidifier 5000

5.5.1 Humidifier Overview

In one form of the present technology there is provided a humidifier 5000 (e.g. as shown in FIG. 6A and FIG. 6B) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 6A and FIG. 6B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6 Glossary

For the purposes of the present technology disclosure, in certain forms of the present technology, one or more of the following definitions may apply. In other forms of the present technology, alternative definitions may apply.

5.6.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g. acoustic) noise may be considered to be the background noise level in the room where a patient is located, other than for example, noise generated by an RPT device or emanating from a mask or patient interface. Ambient noise may be generated by sources outside the room.

5.6.2 Anatomy of the Face

Frankfort horizontal plane: A line extending from the most inferior point of the orbital margin to the left tragion. The tragion is the deepest point in the notch superior to the tragus of the auricle.

Nares (Nostrils): Approximately ellipsoidal apertures forming the entrance to the nasal cavity. The singular form of nares is naris (nostril). The nares are separated by the nasal septum.

5.6.3 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240.

Polycarbonate: a typically transparent thermoplastic polymer of Bisphenol-A Carbonate.

5.6.4 Aspects of a Patient Interface

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Plenum chamber: a plenum chamber will be taken to mean a portion of a patient interface having walls enclosing a volume of space, the volume receiving air prior to delivery through the air directing portion. In some forms, a shell or a frame may form part of the walls of a plenum chamber.

5.6.5 Terms Used in Relation to Patient Interface

5.7 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

5.8 Reference Signs List

| Part | Reference |
| --- | --- |
| patient | 1000 |
| bed partner | 1100 |
| patient interface | 3000 |
| nasal prong | 3100 |
| opening | 3110 |
| barrel | 3150 |
| grip | 3150gr |
| notch | 3152 |
| manifold | 3200 |
| front indent | 3200fi |
| rear indent | 3200ri |
| manifold cap | 3210 |
| Positioning and stabilising structure | 3300 |
| side brace | 3310 |
| cheek engaging region | 3310ch |
| silicone overmould | 3310om |
| skeletal portion | 3310sk |
| front brace | 3320 |
| recess | 3323 |
| central portion | 3325 |
| side portion | 3327 |
| brace | 3330 |
| textile cover | 3330tc |
| central portion | 3335 |
| anchor portion | 3335an |
| end portion | 3335ep |
| strut | 3335st |
| top strap | 3340 |
| rear strap | 3350 |
| connection port | 3600 |
| RPT device | 4000 |
| external housing | 4010 |
| upper portion | 4012 |
| lower portion | 4014 |
| panel | 4015 |
| chassis | 4016 |
| handle | 4018 |
| pneumatic block | 4020 |
| pneumatic component | 4100 |
| inlet air filter | 4112 |
| blower | 4142 |

-continued

| Part | Reference |
| --- | --- |
| air circuit | 4170 |
| electrical component | 4200 |
| PCBA | 4202 |
| electrical power supply | 4210 |
| humidifier | 5000 |
| humidifier inlet | 5002 |
| humidifier outlet | 5004 |
| humidifier base | 5006 |
| humidifier reservoir | 5110 |
| humidifier reservoir dock | 5130 |
| heating element | 5240 |

The invention claimed is:

1. A patient interface for delivery of a flow of air into one or more nares of a patient, the patient interface comprising:
a plenum chamber configured to receive a flow of air;
a prong configured to deliver the flow of air from the plenum chamber into a naris of the patient; and
a frame coupled to the plenum chamber, the frame being configured to engage a head of the patient in use for locating the plenum chamber with respect to the naris of the patient,
wherein the plenum chamber and a central portion of the frame are spaced apart across a recess by a first distance when the plenum chamber and the frame are fully coupled to each other, and
wherein the plenum chamber is configured to, in use, be moved into the recess toward the central portion so that the central portion and the plenum chamber are spaced apart by a second distance less than the first distance.

2. The patient interface of claim 1, wherein the plenum chamber comprises a flexible material, and the frame comprises a rigid material configured to act as a stop for the plenum chamber when the plenum chamber moves into the recess.

3. The patient interface of claim 1, wherein the first distance as measured between a posterior surface of the frame and an exterior surface of the plenum chamber is between approximately 1 mm and 4 mm.

4. The patient interface of claim 1, wherein the frame includes a side portion and a central portion, the side portion of the frame is connected to the plenum chamber proximate to an end of the plenum chamber and limits translation of the end of the plenum chamber in an anterior direction, and the central portion of the frame diverges from the side portion of the frame in order to be disengaged from a central portion of the plenum chamber across the recess, wherein a central portion of the plenum chamber is configured to move in the anterior direction toward the central portion of the frame so that the central portion of the plenum chamber and the central portion of the frame are spaced apart by the second distance.

5. The patient interface of claim 1, further comprising a barrel coupled to the plenum chamber, wherein the barrel is rotatably engaged with the frame in use, and wherein the plenum chamber is rotatable relative to the frame in use.

6. The patient interface of claim 5, wherein the barrel includes one of notches and protrusions and the frame includes the other of the notches and the protrusions, wherein the notches are configured to engage the protrusions so that relative rotation between the frame and the plenum chamber is discretely variable.

* * * * *